US010946078B2

(12) United States Patent
Tars

(10) Patent No.: US 10,946,078 B2
(45) Date of Patent: Mar. 16, 2021

(54) TREATMENT OF CANINE ATOPIC DERMATITIS

(71) Applicant: BENCHMARK ANIMAL HEALTH LTD., Sheffield (GB)

(72) Inventor: Kaspars Tars, Jaunolaine (LV)

(73) Assignee: BENCHMARK ANIMAL HEALTH LTD., Sheffield (GB)

( * ) Notice: Subject to any disclaimer, the term of this patent is extended or adjusted under 35 U.S.C. 154(b) by 0 days.

(21) Appl. No.: 16/097,156

(22) PCT Filed: Apr. 26, 2017

(86) PCT No.: PCT/EP2017/059977
§ 371 (c)(1),
(2) Date: Oct. 26, 2018

(87) PCT Pub. No.: WO2017/186813
PCT Pub. Date: Nov. 2, 2017

(65) Prior Publication Data

US 2019/0209668 A1 Jul. 11, 2019

(30) Foreign Application Priority Data

Apr. 27, 2016 (EP) .................................... 16167264

(51) Int. Cl.

| | |
|---|---|
| ***A61K 39/00*** | (2006.01) |
| ***C12N 7/00*** | (2006.01) |
| ***A61P 37/00*** | (2006.01) |
| ***A61K 39/12*** | (2006.01) |
| ***C07K 16/24*** | (2006.01) |
| ***C07K 14/005*** | (2006.01) |
| ***C07K 14/08*** | (2006.01) |
| ***A61K 39/35*** | (2006.01) |

(52) U.S. Cl.
CPC .......... *A61K 39/0008* (2013.01); *A61K 39/12* (2013.01); *A61K 39/35* (2013.01); *A61P 37/00* (2018.01); *C07K 14/005* (2013.01); *C07K 14/08* (2013.01); *C07K 16/244* (2013.01); *C12N 7/00* (2013.01); *A61K 2039/5256* (2013.01); *A61K 2039/5258* (2013.01); *A61K 2039/552* (2013.01); *C12N 2760/00022* (2013.01); *C12N 2760/00023* (2013.01); *C12N 2760/00034* (2013.01); *C12N 2760/16034* (2013.01); *C12N 2770/14022* (2013.01); *C12N 2770/14023* (2013.01)

(58) Field of Classification Search
None
See application file for complete search history.

(56) References Cited

U.S. PATENT DOCUMENTS

| | | | | |
|---|---|---|---|---|
| 8,465,756 B2 * | 6/2013 | Liu | .................... | A61K 39/0011 424/277.1 |
| 8,790,651 B2 * | 7/2014 | Bammert | ............. | C07K 16/244 424/145.1 |
| 10,532,107 B2 * | 1/2020 | Bachmann | ............. | A61K 39/39 |

FOREIGN PATENT DOCUMENTS

| | | | | |
|---|---|---|---|---|
| WO | 2006/032674 A1 | 3/2006 | | |
| WO | 2016/062720 A1 | 4/2016 | | |
| WO | WO2016062720 * | 4/2016 | ............. | A61K 39/12 |

OTHER PUBLICATIONS

International Search Report issued in International Application No. PCT/EP2017/059977, dated Jul. 25, 2017.
Database UniProt dated Mar. 1, 2001 retrieved from EBI accession No. UniProt:Q9DJX6.
Gellért et al., "A Cucumber Mosaic Virus Based Expression System for the Production of Porcine Circovirus Specific Vaccines," PLoS ONE 7(12):e52688 (2012).
Gonzales et al., "Interleukin-31: its role in canine pruritus and naturally occurring canine atopic dermatitis," Veterinary Dermatology 24:48-e12 (2013).
Grimstad et al., "Anti-interleukin-31-antibodies ameliorate scratching behaviour in NC/Nga mice: a model of atopic dermatitis," Experimental Dermatology 18:35-43 (2008).
Jemon et al., "An Enhanced Heterologous Virus-Like Particle for Human Papillomavirus Type 16 Tumour Immunotherapy," PLoS ONE 8(6):e66866 (2013).
Kasutani et al., "Anti-IL-31 receptor antibody is shown to be a potential therapeutic option for treating itch and dermatitis in mice," British Journal of Pharmacology 171:5049-5058 (2014).
Kaumaya et al., "Peptide Vaccines Incorporating a 'Promiscuous' T-cell Epitope Bypass Certain Haplotype Restricted Immune Responses and Provide Broad Spectrum Immunogenicity," Journal of Molecular Recognition 6:81-94 (1993).
Lewis et al., "Interleukin (IL) 31 induces in cynomolgus monkey a rapid and intense itch response that can be inhibited by an IL-31 neutralizing antibody," JEADV 31:142-150 (2017).
Tissot et al., "Versatile Virus-Like Particle Carrier for Epitope Based Vaccines," PLoS ONE 5(3):e9809 (2010).

* cited by examiner

*Primary Examiner* — Agnieszka Boesen
(74) *Attorney, Agent, or Firm* — Medler Ferro Woodhouse & Mills PLLC

(57) ABSTRACT

The present invention relates to compositions, immunogenic or vaccine compositions and pharmaceutical compositions for the prevention or treatment of canine atopic dermatitis (CAD). Furthermore, the invention provides methods for preventing or treating CAD. The compositions of the invention induce efficient immune responses, in particular antibody responses, in dogs and are, therefore, useful for the treatment and/or prevention of CAD.

19 Claims, 11 Drawing Sheets

Specification includes a Sequence Listing.

| | | | Size (d.nm... | % Volume | Width (d.n... |
|---|---|---|---|---|---|
| Z-Average (d.nm): | 80.92 | Peak 1: | 39.03 | 95.0 | 18.97 |
| PdI: | 0.434 | Peak 2: | 307.8 | 3.9 | 117.9 |
| Intercept: | 0.943 | Peak 3: | 4674 | 1.2 | 924.9 |
| Result quality | Good | | | | |

| | | | Size (d.nm... | % Volume | Width (d.n... |
|---|---|---|---|---|---|
| Z-Average (d.nm): | 61.88 | Peak 1: | 45.98 | 99.5 | 20.78 |
| PdI: | 0.185 | Peak 2: | 4448 | 0.5 | 992.6 |
| Intercept: | 0.959 | Peak 3: | 0.000 | 0.0 | 0.000 |
| Result quality | Good | | | | |

TREATMENT OF CANINE ATOPIC DERMATITIS

NAMES OF THE PARTIES TO A JOINT RESEARCH AGREEMENT

The subject matter of the disclosed invention was made as a result of a joint research agreement between Saiba Animal Health GmbH, Saiba GmbH, and Benchmark Animal Health Limited.

REFERENCE TO AN ELECTRONIC SEQUENCE LISTING

The contents of the electronic sequence listing (0192-0071US1_SL.txt; Size: 28,336 bytes and Date of Creation: Nov. 19, 2018) is herein incorporated by reference in its entirety.

The present invention relates to compositions, immunogenic or vaccine compositions and pharmaceutical compositions for the prevention or treatment of canine atopic dermatitis (CAD). Furthermore, the invention provides methods for preventing or treating CAD. The compositions of the invention induce efficient immune responses, in particular antibody responses, in dogs and are, therefore, useful for the treatment and/or prevention of CAD.

RELATED ART

Canine atopic dermatitis (CAD) is defined as an inflammatory and pruritic allergic skin disease caused by an interaction between genetic and environmental factors and affects up to 10% of all canines (Hensel P et al., (2015) BMC Veterinary Research 11:196-209; Meury S et al., (2011) Vet Dermatol 22: 327-334; Nodtvedt A, et al., (2007) Prey Vet Med 78: 210-222). It is the second most common allergic skin condition in canidae, in particular domestic dogs, surpassed only by flea allergies. The allergic symptoms appear as eczematous skin and canidae such as domestic dogs with atopic dermatitis often suffer from pruritus, or severe itching, hair loss, excoriation of the skin from deep scratching, frequent licking of their paws and excessive tear production. Secondary skin problems are also common, including skin infections and excessive sebum discharge.

Clinical signs usually develop at a young age and the peak age of onset is typically between six months and three years. Face, ears, paws, extremities, ventrum and flex-zones are typically affected by pruritus and erythema (Griffin C E, DeBoer D J (2001) Veterinary Immunology and Immunopathology 81: 255-269). It is typically a chronic relapsing condition and most dogs will require ongoing, usually life-long, therapy (Nuttall T., et al., Veterinary Record (2014) 174 (suppl 2), 3-12).

Several treatments for CAD and pruritus have already been described including the use of antihistamines, such as fexofenadine, or drugs like cyclosporine. A recently approved product known as a Janus kinase, or JAK, inhibitor is also available for treating CAD (Nuttall T., et al., Veterinary Record (2014) 174 (suppl 2), 3-12); WO 2015/042596).

While these drugs seem to be effective, they have significant side effects that can prevent their long-term use. For example, these drugs suppress the canidae's such as domestic dogs' immune system, which can lead to infections. Corticosteroids also can cause osteoporosis, endocrine problems and cataracts in canidae and domestic dogs. In addition, corticosteroids tend to cause canidae such as domestic dogs to eat, drink and urinate frequently, which is considered undesirable by pet owners. Moreover, many of the drugs have to be given orally and daily, which renders their use very inconvenient. As CAD is often a chronic condition, these safety and side effect issues create a significant unmet medical need for a safe and effective long-term treatment. Moreover, not only the safety but compliance is still a further matter of concern. Thus, there remains a need for treatment options for CAD. The present invention meets this need.

SUMMARY OF THE INVENTION

The present invention provides for compositions for the prevention and treatment of atopic dermatitis in canidae, including and preferably of domestic dogs (*Canis lupus familiaris* or *Canis familiaris*), and other members of the family. In particular, the present invention provides for compositions and its uses for prevention and treatment of canine atopic dermatitis (CAD), wherein preferred inventive compositions comprise canine Interleukin-31 antigen (cIL-31 antigen) displayed on virus-like particles of plant virus Cucumber Mosaic Virus (CMV) modified by incorporation of Th cell epitopes, in particular universal Th cell epitopes. Furthermore, these modified VLPs serve as vaccines for generating immune responses, in particular antibody responses, against cIL-31. The presence of the Th cell epitopes, in particular universal Th cell epitopes, leads to a further increase in the generated immune response and, thus, the beneficial effect for the prevention and treatment of CAD.

Thus, the administration of the compositions of the present invention to canidae, in particular domestic dogs, leads to an efficient reduction of CAD disease parameters and symptoms. In particular, the administration of the compositions of the present invention to canidae, in particular domestic dogs, not only leads to the induction of autoantibodies and reduction of interleukin 31 levels in blood and skin of the canidae, in particular domestic dogs, but furthermore said reduction of cIL-31 levels correlates with reduction of CAD disease symptoms. Moreover, the administration of the compositions of the present invention to canidae, in particular domestic dogs, leads to reduced itching and an efficient reduction of the severity grade of skin lesions of the dogs affected with CAD.

Treatment in accordance with the invention results in a lowering of the Atopic Dermatitis Lesion Index, or ADLI, and Pruritus Visual Analog Score, or PVAS in treated canidae, in particular domestic dogs. The ADLI score is a validated composite index of six clinical symptoms associated with canine atopic dermatitis evaluated in five specified body regions. At each specified body region, each parameter is scored by the scorer from zero to five, with a score of zero defined as no lesion and a score of five defined as a severe/extensive lesions. PVAS is scored by the scorer using a zero to ten analog scale, with a score of zero representing no pruritus/chewing and a score of ten equating to incessant and intense pruritus/chewing.

Without being bound by this explanation, the present invention is believed to impact on CAD which is considered to be a multifaceted disease. It is believed that in CAD, the combination of Th2 polarization and microbial presence may lead to cIL-31 mediated effects driving inflammation and pruritus by immune cells, keratinocytes, and direct neuronal stimulation causing itching. The induced autoantibodies to cIL-31 by the compositions and methods of the present invention in canidae such as and in particular domestic dogs, thus, reduce the levels of cIL-31 and thus, have a positive impact on CAD by reducing itching and consequently scratching of the dog, inhibiting all the downstream events of scratching, including inflammation and infection.

Thus, in a first aspect, the present invention provides for a composition for use in a method of preventing or treating canine atopic dermatitis (CAD) of a canidae, preferably of a domestic dog, wherein an effective amount of said composition is administered to said canidae, preferably to said domestic dog, and wherein said composition comprises (a) a core particle with at least one first attachment site; and (b) at least one canine Interleukin-31 antigen (cIL-31 antigen) with at least one second attachment site, wherein said cIL-31 antigen comprises, or preferably consists of, a protein with the amino sequence selected from SEQ ID NO:22 or a protein with an amino acid sequence of at least 90%, preferably of at least 92%, further preferably of at least 95%, and again further preferably of at least 98% amino acid sequence identity with SEQ ID NO:22; wherein (a) and (b) are linked through said at least one first and said at least one second attachment site via at least one non-peptide covalent bond.

In a preferred embodiment, said core particle is a virus-like particle (VLP), preferably a recombinant VLP. In a further preferred embodiment, said VLP is a modified VLP of cucumber mosaic virus (CMV), wherein said modified VLP of CMV comprises, essentially consists of, or alternatively consists of, at least one modified CMV polypeptide, wherein said modified CMV polypeptide comprises, or preferably consists of, (a) a CMV polypeptide, and (b) a T helper cell epitope; and wherein said CMV polypeptide comprises, or preferably consists of, (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%. In a further very preferred embodiment, said CMV polypeptide comprises, or preferably consists of, (a) an amino acid sequence of a coat protein of CMV, wherein said amino acid sequence comprises, or preferably consists of, SEQ ID NO:1 or (b) an amino acid sequence having a sequence identity of at least 90% of SEQ ID NO:1; and wherein said amino sequence as defined in (a) or (b) in this claim comprises SEQ ID NO:23; or wherein said amino sequence as defined in (a) or (b) in this claim comprises an amino acid sequence region, wherein said amino acid sequence region has a sequence identity of at least 90% with SEQ ID NO:23. In a further very preferred embodiment, said VLP is a modified VLP of cucumber mosaic virus (CMV), wherein said modified CMV polypeptide comprises, preferably consists of, an amino acid sequence of SEQ ID NO:6 or SEQ ID NO:7.

In a further very preferred embodiment, said at least one cIL-31 antigen comprises, or preferably consists of, a protein with the amino sequence selected from: (a) SEQ ID NO:18; (b) SEQ ID NO:21; (c) SEQ ID NO:22; or (d) SEQ ID NOs:25-30. In a further very preferred embodiment, said at least one cIL-31 antigen comprises, or preferably consists of, a protein with the amino sequence selected from: (a) SEQ ID NO:18; (b) SEQ ID NO:21; (c) SEQ ID NO:22; (d) SEQ ID NO:25 or (e) SEQ ID NO:26. In a further very preferred embodiment, said second attachment site is a sulfhydryl group, and wherein preferably said sulfhydryl group is derived from reaction of said cIL-31 antigen with N-succinimidyl S-acetylthioacetate (SATA). In a further very preferred embodiment, said second attachment site is a sulfhydryl group, and wherein preferably said sulfhydryl group is derived from reaction of a lysine residue of said cIL-31 antigen.

In a further aspect, the present invention provides for an immunogenic or vaccine composition comprising an effective amount of said composition of the invention, wherein preferably said immunogenic or vaccine composition further comprises an adjuvant.

In a further aspect, the present invention provides for a pharmaceutical composition comprising: (a) the inventive composition or the inventive immunogenic or vaccine composition; and (b) a pharmaceutically acceptable carrier.

In a further aspect, the present invention provides for a method of immunization, wherein said method comprises administering the inventive composition, the inventive immunogenic or vaccine composition or the inventive pharmaceutical composition to human.

In a further aspect, the present invention provides for the inventive composition, the inventive immunogenic or vaccine composition, or the inventive pharmaceutical composition for use as a medicament.

In a further aspect, the present invention provides for the inventive composition, the inventive immunogenic or vaccine composition, or the inventive pharmaceutical composition for use in a method of prevention or treatment of canine atopic dermatitis (CAD) of a domestic dog, wherein an effective amount of said inventive composition, said inventive immunogenic or vaccine composition, or said inventive pharmaceutical composition is administered to said domestic dog. Preferably, said administration of said inventive composition, said inventive immunogenic or vaccine composition, or said inventive pharmaceutical composition reduces at least one symptom of said canine atopic dermatitis (CAD) when compared to the at least one symptom before said administration.

In a further aspect, the present invention provides for a method of prevention or treatment of canine atopic dermatitis (CAD) of a domestic dog, wherein said method comprises administering an effective amount of said inventive composition, said inventive immunogenic or vaccine composition, or said inventive pharmaceutical composition to said domestic dog.

In another aspect, the present invention provides for the use of said inventive composition, said inventive immunogenic or vaccine composition, or said inventive pharmaceutical composition for the manufacture of a medicament for the prevention or treatment of canine atopic dermatitis (CAD) of a domestic dog, wherein typically and preferably an effective amount of said inventive composition, said inventive immunogenic or vaccine composition, or said inventive pharmaceutical composition is administered to said domestic dog.

In another aspect, the present invention provides for the present invention provides for a composition for use in a method of preventing or treating canine atopic dermatitis (CAD) of a domestic dog, wherein an effective amount of said composition is administered to said domestic dog, and wherein said composition comprises (a) a core particle with at least one first attachment site, wherein said core particle is preferably a virus-like particle (VLP), further preferably a recombinant VLP; and (b) at least one canine Interleukin-31 antigen (cIL-31 antigen) with at least one second attachment site, wherein said cIL-31 antigen comprises, or preferably consists of, a protein with the amino sequence selected from SEQ ID NO:22 or a protein with an amino acid sequence of at least 90%, preferably of at least 92%, further preferably of at least 95%, and again further preferably of at least 98% amino acid sequence identity with SEQ ID NO:22; wherein (a) and (b) are linked through said at least one first and said at least one second attachment site via at least one non-peptide covalent bond.

In a further aspect, the present invention provides for a composition comprising (a) a virus-like particle (VLP) with at least one first attachment site; (b) at least one canine Interleukin-31 antigen (cIL-31 antigen) with at least one second attachment site, wherein said cIL-31 antigen comprises, or preferably consists of, a protein with the amino sequence selected from SEQ ID NO:22 or a protein with an amino acid sequence of at least 90%, preferably of at least 92%, further preferably of at least 95%, and again further preferably of at least 98% amino acid sequence identity with SEQ ID NO:22, and again further preferably said antigen comprises, or preferably consists of a protein with the amino sequence of SEQ ID NO:22; wherein (a) and (b) are linked through said at least one first and said at least one second attachment site via at least one non-peptide covalent bond.

In a further very preferred embodiment, said VLP is a modified VLP of cucumber mosaic virus (CMV), wherein said modified CMV polypeptide comprises, preferably consists of, an amino acid sequence of SEQ ID NO:6 or SEQ ID NO:7.

In a further very preferred embodiment, said at least one cIL-31 antigen comprises, or preferably consists of, a protein with the amino sequence selected from: (a) SEQ ID NO:18; (b) SEQ ID NO:21; (c) SEQ ID NO:22; or (d) SEQ ID NOs:25-30. In a further very preferred embodiment, said at least one cIL-31 antigen comprises, or preferably consists of, a protein with the amino sequence selected from: (a) SEQ ID NO:18; (b) SEQ ID NO:21; (c) SEQ ID NO:22; (d) SEQ ID NO:25 or (e) SEQ ID NO:26. In a further very preferred embodiment, said second attachment site is a sulfhydryl group, and wherein preferably said sulfhydryl group is derived from reaction of said cIL-31 antigen with N-succinimidyl S-acetylthioacetate (SATA). In a further very preferred embodiment, said second attachment site is a sulfhydryl group, and wherein preferably said sulfhydryl group is derived from reaction of a lysine residue of said cIL-31 antigen.

Further aspects and embodiments of the present invention will be become apparent as this description continues.

BRIEF DESCRIPTION OF FIGURES

FIG. 3 Mass spectrometric analysis of purified CMV-derived VLPs. Matrix-assisted laser desorption/ionization (MALDI)-TOF MS analysis was carried out on an Autoflex MS (Bruker Daltonik, Germany). The protein molecular mass (MM) calibration standard II (22.3-66.5 kDa; Bruker Daltonik) was used for mass determination.

DETAILED DESCRIPTION OF THE INVENTION

Figure 1:
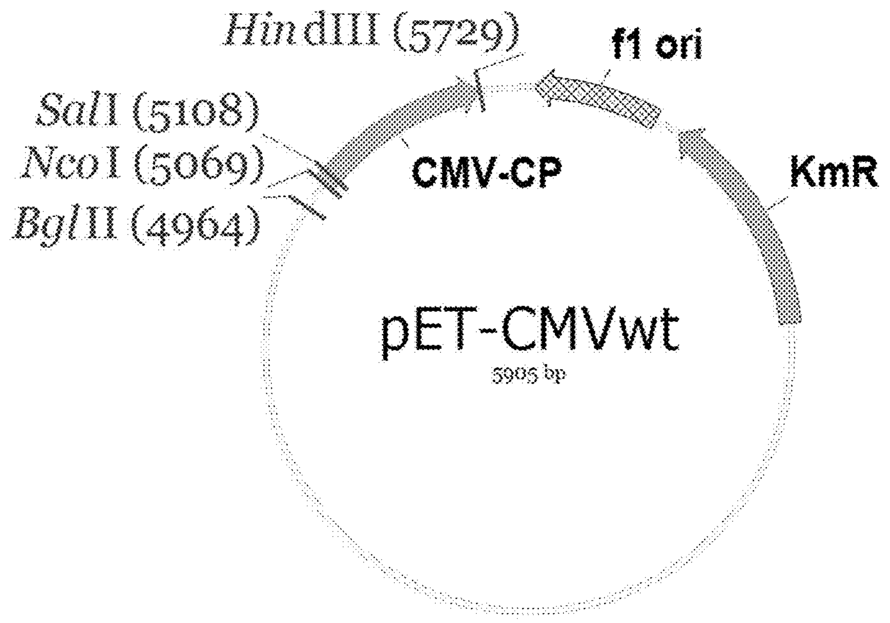
FIG. 1 pET-CMVwt plasmid map. The relative positions of relevant genes and restriction enzyme sites are denoted.

Unless defined otherwise, all technical and scientific terms used herein have the same meanings as commonly understood by one of ordinary skill in the art to which this invention belongs.

Virus-like particle (VLP): The term "virus-like particle (VLP)" as used herein, refers to a non-replicative or non-infectious, preferably a non-replicative and non-infectious virus particle, or refers to a non-replicative or non-infectious, preferably a non-replicative and non-infectious structure resembling a virus particle, preferably a capsid of a virus. The term "non-replicative", as used herein, refers to being incapable of replicating the genome comprised by the VLP. The term "non-infectious", as used herein, refers to being incapable of entering the host cell. A virus-like particle in accordance with the invention is non-replicative and non-infectious since it lacks all or part of the viral genome or genome function. A virus-like particle in accordance with the invention may contain nucleic acid distinct from their genome. Recombinantly produced virus-like particles typically contain host cell derived RNA. A typical and preferred embodiment of a virus-like particle in accordance with the present invention is a viral capsid composed of polypeptides of the invention. A virus-like particle is typically a macromolecular assembly composed of viral coat protein which typically comprises 60, 120, 180, 240, 300, 360, or more than 360 protein subunits per virus-like particle. Typically and preferably, the interactions of these subunits lead to the formation of viral capsid or viral-capsid like structure with an inherent repetitive organization. One feature of a virus-like particle is its highly ordered and repetitive arrangement of its subunits.

Virus-like particle of CMV: The terms "virus-like particle of CMV" or CMV VLPs refer to a virus-like particle comprising, or preferably consisting essentially of, or preferably consisting of at least one CMV polypeptide. Preferably, a virus-like particle of CMV comprises said CMV polypeptide as the major, and even more preferably as the sole protein component of the capsid structure. Typically and preferably, virus-like particles of CMV resemble the structure of the capsid of CMV. Virus-like particles of CMV are non-replicative and/or non-infectious, and lack at least the gene or genes encoding for the replication machinery of the CMV, and typically also lack the gene or genes encoding the protein or proteins responsible for viral attachment to or entry into the host. This definition includes also virus-like particles in which the aforementioned gene or genes are still present but inactive. Preferred methods to render a virus-like particle of CMV non replicative and/or non-infectious is by physical or chemical inactivation, such as UV irradiation, formaldehyde treatment. Preferably, VLPs of CMV lack the gene or genes encoding for the replication machinery of the CMV, and also lack the gene or genes encoding the protein or proteins responsible for viral attachment to or entry into the host. Again more preferably, non-replicative and/or non-infectious virus-like particles are obtained by recombinant gene technology. Recombinantly produced virus-like particles of CMV according to the invention typically and preferably do not comprise the viral genome. Virus-like particles comprising more than one species of polypeptides, often referred to as mosaic VLPs are also encompassed by the invention. Thus, in one embodiment, the virus-like particle according to the invention comprises at least two different species of polypeptides, wherein at least one of said species of polypeptides is a CMV polypeptide. Preferably, a VLP of CMV is a macromolecular assembly composed of CMV coat protein which typically comprises 180 coat protein subunits per VLP. Typically and preferably, a VLP of CMV as used herein, comprises, essentially consists of, or alternatively consists of, at least one CMV polypeptide comprising or preferably consisting of (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said amino acid sequence to be mutated show a sequence identity of at least 90%, preferably of at least 95%, further preferably of at least 98% and again more preferably of at least 99%.

Polypeptide: The term "polypeptide" as used herein refers to a polymer composed of amino acid monomers which are linearly linked by peptide bonds (also known as amide bonds). The term polypeptide refers to a consecutive chain of amino acids and does not refer to a specific length of the product. Thus, peptides, and proteins are included within the definition of polypeptide.

Cucumber Mosaic Virus (CMV) polypeptide: The term "cucumber mosaic virus (CMV) polypeptide" as used herein refers to a polypeptide comprising or preferably consisting of: (i) an amino acid sequence of a coat protein of cucumber mosaic virus (CMV), or (ii) a mutated amino acid sequence, wherein the amino acid sequence to be mutated is an amino acid sequence of a coat protein of CMV, and wherein said mutated amino acid sequence and said amino acid sequence to be mutated, i.e. said coat protein of CMV, show a sequence identity of at least 90%, preferably of at least 95%, further preferably of at least 98% and again more preferably of at least 99%. Typically and preferably, the CMV polypeptide is capable of forming a virus-like particle of CMV upon expression by self-assembly.

Coat protein (CP) of cucumber mosaic virus (CMV): The term "coat protein (CP) of cucumber mosaic virus (CMV)", as used herein, refers to a coat protein of the cucumber mosaic virus which occurs in nature. Due to extremely wide host range of the cucumber mosaic virus, a lot of different strains and isolates of CMV are known and the sequences of the coat proteins of said strains and isolates have been determined and are, thus, known to the skilled person in the art as well. The sequences of said coat proteins (CPs) of CMV are described in and retrievable from the known databases such as Genbank, www.dpvweb.net, or www.ncbi.nlm.nih.gov/protein/. Examples are described in EP Application No. 14189897.3. Further examples of CMV coat proteins are provided in SEQ ID NOs 1-3. It is noteworthy that these strains and isolates have highly similar coat protein sequences at different protein domains, including the N-terminus of the coat protein. In particular, 98.1% of all completely sequenced CMV isolates share more than 85% sequence identity within the first 28 amino acids of their coat protein sequence, and still 79.5% of all completely sequenced CMV isolates share more than 90% sequence identity within the first 28 amino acids of their coat protein sequence.

Typically and preferably, the coat protein of CMV used for the present invention is capable of forming a virus-like particle of CMV upon expression by self-assembly. Preferably, the coat protein of CMV used for the present invention is capable of forming a virus-like particle of CMV upon expression by self-assembly in *E. coli*.

Modified virus-like particle (VLP) of cucumber mosaic virus (CMV): The term "modified virus-like particle (VLP) of cucumber mosaic virus (CMV)" as used herein, refers to a VLP of CMV which is a modified one in such as it comprises, or preferably consists essentially of, or preferably consists of at least one modified CMV polypeptide, wherein said modified CMV polypeptide comprises, or preferably consists of, a CMV polypeptide, and a T helper cell epitope. Typically and preferably, said T helper cell epitope (i) is fused to the N-terminus of said CMV polypeptide, (ii) is fused to the C-terminus of said CMV polypeptide, (iii) replaces a region of consecutive amino acids of said CMV polypeptide, wherein the sequence identity between said replaced region of consecutive amino acids of said CMV polypeptide and the T helper cell epitope is at least 15%, preferably at least 20%, or (iv) replaces a N-terminal region of said CMV polypeptide, and wherein said replaced N-terminal region of said CMV polypeptide consists of 5 to 15 consecutive amino acids. Preferably, said T helper cell epitope replaces a N-terminal region of said CMV polypeptide, and wherein said replaced N-terminal region of said CMV polypeptide consists of 5 to 15 consecutive amino acids, preferably of 9 to 14 consecutive amino acids, more preferably of 11 to 13 consecutive amino acids, and most preferably of 11, 12 or 13 consecutive amino acids. Preferably said modified VLP of CMV of the present invention is a recombinant modified VLP of CMV.

Modified CMV polypeptide: The term "modified CMV polypeptide" as used herein refers to a CMV polypeptide modified in such as defined herein, that said modified CMV polypeptide comprises, or preferably consists of, a CMV polypeptide, and a T helper cell epitope. Typically, the modified CMV polypeptide is capable of forming a virus-like particle of CMV upon expression by self-assembly. Preferably, the modified CMV polypeptide is a recombinant modified CMV polypeptide and is capable of forming a virus-like particle of CMV upon expression by self-assembly in *E. coli*.

N-terminal region of the CMV polypeptide: The term "N-terminal region of the CMV polypeptide" as used herein, refers either to the N-terminus of said CMV polypeptide, and in particular to the N-terminus of a coat protein of CMV, or to the region of the N-terminus of said CMV polypeptide or said coat protein of CMV but starting with the second amino acid of the N-terminus of said CMV polypeptide or said coat protein of CMV if said CMV polypeptide or said coat protein comprises a N-terminal methionine residue. Preferably, in case said CMV polypeptide or said coat protein comprises a N-terminal methionine residue, from a practical point of view, the start-codon encoding methionine will usually be deleted and added to the N-terminus of the Th cell epitope. Further preferably, one, two or three additional amino acids, preferably one amino acid, may be optionally inserted between the stating methionine and the Th cell epitope for cloning purposes. The term "N-terminal region of the mutated amino acid sequence of a CMV polypeptide or a CMV coat protein" as used herein, refers either to the N-terminus of said mutated amino acid sequence of said CMV polypeptide or said coat protein of CMV, or to the region of the N-terminus of said mutated amino acid sequence of said CMV polypeptide or said coat protein of CMV but starting with the second amino acid of the N-terminus of said mutated amino acid sequence of said CMV polypeptide or said coat protein of CMV if said mutated amino acid sequence comprises a N-terminal methionine residue. Preferably, in case said CMV polypeptide or said coat protein comprises a N-terminal methionine residue, from a practical point of view, the start-codon encoding methionine will usually be deleted and added to the N-terminus of the Th cell epitope. Further preferably, one, two or three additional amino acids, preferably one amino acid, may be optionally inserted between the stating methionine and the Th cell epitope for cloning purposes.

Recombinant polypeptide: In the context of the invention the term "recombinant polypeptide" refers to a polypeptide which is obtained by a process which comprises at least one step of recombinant DNA technology. Typically and preferably, a recombinant polypeptide is produced in a prokaryotic expression system. It is apparent for the artisan that recombinantly produced polypeptides which are expressed in a prokaryotic expression system such as *E. coli* may comprise an N-terminal methionine residue. The N-terminal methionine residue is typically cleaved off the recombinant polypeptide in the expression host during the maturation of the recombinant polypeptide. However, the cleavage of the N-terminal methionine may be incomplete. Thus, a preparation of a recombinant polypeptide may comprise a mixture of otherwise identical polypeptides with and without an N-terminal methionine residue. Typically and preferably, a preparation of a recombinant polypeptide comprises less than 10%, more preferably less than 5%, and still more preferably less than 1% recombinant polypeptide with an N-terminal methionine residue.

Recombinant CMV polypeptide: The term "recombinant CMV polypeptide" refers to a CMV polypeptide as defined above which is obtained by a process which comprises at least one step of recombinant DNA technology. Typically and preferably a preparation of a recombinant CMV polypeptide comprises less than 10%, more preferably less than 5%, and still more preferably less than 1% recombinant CMV polypeptide with an N-terminal methionine residue. Consequently, a recombinant virus-like particle of the invention may comprise otherwise identical recombinant polypeptides with and without an N-terminal methionine residue.

Recombinant modified CMV polypeptide: The term "recombinant modified CMV polypeptide" refers to a modified CMV polypeptide as defined above which is obtained by a process which comprises at least one step of recombinant DNA technology. Typically and preferably a preparation of a recombinant modified CMV polypeptide comprises less than 10%, more preferably less than 5%, and still more preferably less than 1% recombinant modified CMV polypeptide with an N-terminal methionine residue. Consequently, a recombinant virus-like particle of the invention may comprise otherwise identical recombinant polypeptides with and without an N-terminal methionine residue.

Recombinant virus-like particle: In the context of the invention the term "recombinant virus-like particle" refers to a virus-like particle (VLP) which is obtained by a process which comprises at least one step of recombinant DNA technology. Typically and preferably, a recombinant virus-like particle comprises at least one recombinant polypeptide, preferably a recombinant CMV polypeptide or recombinant modified CMV polypeptide. Most preferably, a recombinant virus-like particle is composed of or consists of recombinant CMV polypeptides or recombinant modified CMV polypeptides. As a consequence, if in the context of the present invention the definition of inventive recombinant VLPs are effected with reference to specific amino acid sequences comprising a N-terminal methionine residue the scope of these inventive recombinant VLPs encompass the VLPs formed by said specific amino acid sequences without said N-terminal methionine residue but as well, even though typically in a minor amount as indicated herein, the VLPs formed by said specific amino acid sequences with said N-terminal methionine. Furthermore, it is within the scope of the present invention that if the definition of inventive recombinant VLPs are effected with reference to specific amino acid sequences comprising a N-terminal methionine residue VLPs are encompassed comprising both amino acid sequences comprising still said N-terminal methionine residue and amino acid sequences lacking the N-terminal methionine residue.

Mutated amino acid sequence: The term "mutated amino acid sequence" refers to an amino acid sequence which is obtained by introducing a defined set of mutations into an amino acid sequence to be mutated. In the context of the invention, said amino acid sequence to be mutated typically and preferably is an amino acid sequence of a coat protein of CMV. Thus, a mutated amino acid sequence differs from an amino acid sequence of a coat protein of CMV in at least one amino acid residue, wherein said mutated amino acid sequence and said amino acid sequence to be mutated show a sequence identity of at least 90%. Typically and preferably said mutated amino acid sequence and said amino acid sequence to be mutated show a sequence identity of at least 91%, 92%, 93% 94%, 95%, 96%, 97%, 98%, or 99%. Preferably, said mutated amino acid sequence and said sequence to be mutated differ in at most 11, 10, 9, 8, 7, 6, 4, 3, 2, or 1 amino acid residues, wherein further preferably said difference is selected from insertion, deletion and amino acid exchange. Preferably, the mutated amino acid sequence differs from an amino acid sequence of a coat protein of CMV in least one amino acid, wherein preferably said difference is an amino acid exchange.

Position corresponding to residues . . . : The position on an amino acid sequence, which is corresponding to given residues of another amino acid sequence can be identified by sequence alignment, typically and preferably by using the BLASTP algorithm, most preferably using the standard settings. Typical and preferred standard settings are: expect threshold: 10; word size: 3; max matches in a query range: 0; matrix: BLOSUM62; gap costs: existence 11, extension 1; compositional adjustments: conditional compositional score matrix adjustment.

Sequence identity: The sequence identity of two given amino acid sequences is determined based on an alignment of both sequences. Algorithms for the determination of sequence identity are available to the artisan. Preferably, the sequence identity of two amino acid sequences is determined using publicly available computer homology programs such as the "BLAST" program (http://blast.ncbi.nlm.nih.gov/Blast.cgi) or the "CLUSTALW" (http://www.genome.jp/tools/clustalw/), and hereby preferably by the "BLAST" program provided on the NCBI homepage at http://blast.ncbi.nlm.nih.gov/Blast.cgi, using the default settings provided therein. Typical and preferred standard settings are: expect threshold: 10; word size: 3; max matches in a query range: 0; matrix: BLOSUM62; gap costs: existence 11, extension 1; compositional adjustments: conditional compositional score matrix adjustment.

Amino acid exchange: The term amino acid exchange refers to the exchange of a given amino acid residue in an amino acid sequence by any other amino acid residue having a different chemical structure, preferably by another proteinogenic amino acid residue. Thus, in contrast to insertion or deletion of an amino acid, the amino acid exchange does not change the total number of amino acids of said amino acid sequence. Very preferred in the context of the invention is the exchange of an amino acid residue of said amino acid sequence to be mutated by a lysine residue or by a cysteine residue.

Epitope: The term epitope refers to continuous or discontinuous portions of an antigen, preferably a polypeptide, wherein said portions can be specifically bound by an antibody or by a T-cell receptor within the context of an MHC molecule. With respect to antibodies, specific binding excludes non-specific binding but does not necessarily exclude cross-reactivity. An epitope typically comprise 5-20 amino acids in a spatial conformation which is unique to the antigenic site.

T helper (Th) cell epitope: The term "T helper (Th) cell epitope" as used herein refers to an epitope that is capable of recognition by a helper Th cell. In another preferred embodiment, said T helper cell epitope is a universal T helper cell epitope.

Universal Th cell epitope: The term "universal Th cell epitope" as used herein refers to a Th cell epitope that is capable of binding to at least one, preferably more than one MHC class II molecules. The simplest way to determine whether a peptide sequence is a universal Th cell epitope is to measure the ability of the peptide to bind to individual MHC class II molecules. This may be measured by the ability of the peptide to compete with the binding of a known Th cell epitope peptide to the MHC class II molecule. A representative selection of HLA-DR molecules are described in e.g. Alexander J, et al., Immunity (1994) 1:751-761. Affinities of Th cell epitopes for MHC class II molecules should be at least $10^{-5}$M. An alternative, more tedious but also more relevant way to determine the "universality" of a Th cell epitope is the demonstration that a larger fraction of people (>30%) generate a measurable T cell response upon immunization and boosting one months later with a protein containing the Th cell epitope formulated in IFA. A representative collection of MHC class II molecules present in different individuals is given in Panina-Bordignon P, et al., Eur J Immunol (1989) 19:2237-2242. As a consequence, the term "universal Th cell epitope" as used herein preferably refers to a Th cell epitope that generates a measurable T cell response upon immunization and boosting (one months later with a protein containing the Th cell epitope formulated in IFA) in more than 30% of a selected group of individuals as described in Panina-Bordignon P, et al., Eur J Immunol (1989) 19:2237-2242. Moreover, and again further preferred, the term "universal Th cell epitope" as used herein preferably refers to a Th cell epitope that is capable of binding to at least one, preferably to at least two, and even more preferably to at least three DR alleles selected from of DR1, DR2w2b, DR3, DR4w4, DR4w14, DR5, DR7, DR52a, DRw53, DR2w2a; and preferably selected from DR1, DR2w2b, DR4w4, DR4w14, DR5, DR7, DRw53, DR2w2a, with an affinity at least 500 nM (as described in Alexander J, et al., Immunity (1994) 1:751-761 and references cited herein); a preferred binding assay to evaluate said affinities is the one described by Sette A, et al., J Immunol (1989) 142:35-40. In an even again more preferable manner, the term "universal Th cell epitope" as used herein refers to a Th cell epitope that is capable of binding to at least one, preferably to at least two, and even more preferably to at least three DR alleles selected from DR1, DR2w2b, DR4w4, DR4w14, DR5, DR7, DRw53, DR2w2a, with an affinity at least 500 nM (as described in Alexander J, et al., Immunity (1994) 1:751-761 and references cited herein); a preferred binding assay to evaluate said affinities is the one described by Sette A, et al., J Immunol (1989) 142:35-40.

Universal Th cell epitopes are described, and known to the skilled person in the art, such as by Alexander J, et al., Immunity (1994) 1:751-761, Panina-Bordignon P, et al., Eur J Immunol (1989) 19:2237-2242, Calvo-Calle J M, et al., J Immunol (1997) 159:1362-1373, and Valmori D, et al., J Immunol (1992) 149:717-721.

Adjuvant: The term "adjuvant" as used herein refers to non-specific stimulators of the immune response or substances that allow generation of a depot in the host which when combined with the vaccine and pharmaceutical composition, respectively, of the present invention may provide for an even more enhanced immune response. Preferred adjuvants are complete and incomplete Freund's adjuvant, aluminum containing adjuvant, preferably aluminum hydroxide, and modified muramyldipeptide. Further preferred adjuvants are mineral gels such as aluminum hydroxide, surface active substances such as lyso lecithin, pluronic polyols, polyanions, peptides, oil emulsions, keyhole limpet hemocyanins, dinitrophenol, and human adjuvants such as BCG (bacille Calmette Guerin) and *Corynebacterium parvum*. Such adjuvants are also well known in the art. Further adjuvants that can be administered with the compositions of the invention include, but are not limited to, Monophosphoryl lipid immunomodulator, AdjuVax 100a, QS-21, QS-18, CRL1005, Aluminum salts (Alum), MF-59, OM-174, OM-197, OM-294, and Virosomal adjuvant technology. The adjuvants may also comprise mixtures of these substances. Virus-like particles have been generally described as an adjuvant. However, the term "adjuvant", as used within the context of this application, refers to an adjuvant not being the inventive virus-like particle. Rather "adjuvant" relates to an additional, distinct component of the inventive compositions, vaccines or pharmaceutical compositions.

Effective amount: As used herein, the term "effective amount" refers to an amount necessary or sufficient to realize a desired biologic effect. An effective amount of the composition, or alternatively the pharmaceutical composition, would be the amount that achieves this selected result, and such an amount could be determined as a matter of routine by a person skilled in the art. Preferably, the term "effective amount", as used herein, refers to an amount necessary or sufficient to be effective to reduce levels of cIL-31 to a level that causes reduced itching in dogs and improves CAD. Preferably, the term "effective amount", as used herein, refers to an amount necessary or sufficient to be effective to neutralize the activity of cIL-31 at sites of inflammation. The effective amount can vary depending on the particular composition being administered and the size of the subject. One of ordinary skill in the art can empirically determine the effective amount of a particular composition of the present invention without necessitating undue experimentation.

Treatment: As used herein, the terms "treatment", "treat", "treated" or "treating" refer to prophylaxis and/or therapy. In one embodiment, the terms "treatment", "treat", "treated" or "treating" refer to a therapeutic treatment. In another embodiment, the terms "treatment", "treat", "treated" or "treating" refer to a prophylactic treatment.

Attachment Site, First: As used herein, the phrase "first attachment site" refers to an element which is naturally occurring with the virus-like particle or which is artificially added to the virus-like particle, and to which the second attachment site may be linked. The first attachment site preferably is a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the first attachment site is the amino group of an amino acid residue, preferably of a lysine residue. The first attachment site is typically located on the surface, and preferably on the outer surface of the VLP. Multiple first attachment sites are present on the surface, preferably on the outer surface of the VLP, typically in a repetitive configuration. In a preferred embodiment the first attachment site is associated with the VLP, through at least one covalent bond, preferably through at least one peptide bond. In a further preferred embodiment the first attachment site is naturally occurring with the VLP. Alternatively, in a preferred embodiment the first attachment site is artificially added to the VLP. In a very preferred embodiment said first attachment site is the amino group of a lysine residue of the amino acid sequence of said VLP polypeptide.

Attachment Site, Second: As used herein, the phrase "second attachment site" refers to an element which is naturally occurring with or which is artificially added to the cIL-31 antigen, and to which the first attachment site may be linked. The second attachment site of the cIL-31 antigen preferably is a protein, a polypeptide, a peptide, an amino acid, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the second attachment site is a sulfhydryl group, preferably the sulfhydryl group of the amino acid cysteine most preferably the sulfhydryl group of a cysteine residue. The term "antigen with at least one second attachment site" or "cIL-31 antigen with at least one second attachment site" refers, therefore, to a construct comprising the cIL-31 antigen and at least one second attachment site. However, in particular for a second attachment site, which is not naturally occurring within the cIL-31 antigen, such a construct typically and preferably further comprises a "linker". In another preferred embodiment the second attachment site is associated with the cIL-31 antigen through at least one covalent bond, preferably through at least one peptide bond. In a further embodiment, the second attachment site is naturally occurring within the cIL-31 antigen. In another further very preferred embodiment, the second attachment site is artificially added to the cIL-31 antigen through a linker, wherein said linker comprises or alternatively consists of a cysteine. Preferably, the linker is fused to the cIL-31 antigen by a peptide bond or is added by chemical linkage.

Linked: The terms "linked" or "linkage" as used herein, refer to all possible ways, preferably chemical interactions, by which the at least one first attachment site and the at least one second attachment site are joined together. Chemical interactions include covalent and non-covalent interactions. Typical examples for non-covalent interactions are ionic interactions, hydrophobic interactions or hydrogen bonds, whereas covalent interactions are based, by way of example, on covalent bonds such as ester, ether, phosphoester, carbon-phosphorus bonds, carbon-sulfur bonds such as thioether, or imide bonds. In certain preferred embodiments the first attachment site and the second attachment site are linked through at least one covalent bond, preferably through at least one non-peptide bond, and even more preferably through exclusively non-peptide bond(s). The term "linked" as used herein, however, shall not only refer to a direct linkage of the at least one first attachment site and the at least one second attachment site but also, alternatively and preferably, an indirect linkage of the at least one first attachment site and the at least one second attachment site through intermediate molecule(s), and hereby typically and preferably by using at least one, preferably one, heterobifunctional cross-linker. In other preferred embodiments the first attachment site and the second attachment site are linked through at least one covalent bond, preferably through at least one peptide bond, and even more preferably through exclusively peptide bond(s).

Linker: A "linker", as used herein, either associates the second attachment site with the cIL-31 antigen or already comprises, essentially consists of, or consists of the second attachment site. Preferably, a "linker", as used herein, already comprises the second attachment site, typically and preferably—but not necessarily—as one amino acid residue, preferably as a cysteine residue. A preferred linkers are an amino acid linkers, i.e. linkers containing at least one amino acid residue. The term amino acid linker does not imply that such a linker consists exclusively of amino acid residues. However, a linker consisting exclusively of amino acid residues is a preferred embodiment of the invention. The amino acid residues of the linker are, preferably, composed of naturally occurring amino acids or unnatural amino acids known in the art, all-L or all-D or mixtures thereof. Further preferred embodiments of a linker in accordance with this invention are molecules comprising a sulfhydryl group or a cysteine residue and such molecules are, therefore, also encompassed within this invention. Association of the linker with the cIL-31 antigen is preferably by way of at least one covalent bond, more preferably by way of at least one peptide bond.

Ordered and repetitive antigen array: As used herein, the term "ordered and repetitive antigen array" refers to a repeating pattern of cIL-31 antigens which typically and preferably is characterized by a high order of uniformity in spacial arrangement of said antigens with respect to the core particle and VLP, respectively. In one embodiment of the invention, the repeating pattern may be a geometric pattern. Preferred ordered and repetitive antigen arrays, moreover, possess strictly repetitive para-crystalline orders of cIL-31 antigens, preferably with spacing of 1 to 30 nanometers, preferably 2 to 15 nanometers, even more preferably 2 to 10 nanometers, even again more preferably 2 to 8 nanometers, and further more preferably 1.6 to 7 nanometers.

Immunostimulatory substance: As used herein, the term "immunostimulatory substance" refers to a substance capable of inducing and/or enhancing an immune response. Immunostimulatory substances, as used herein, include, but are not limited to, toll-like receptor activating substances and substances inducing cytokine secretion. Toll-like receptor activating substances include, but are not limited to, immunostimulatory nucleic acids, peptideoglycans, lipopolysaccharides, lipoteichonic acids, imidazoquinoline compounds, flagellins, lipoproteins, and immuno stimulatory organic substances such as taxol.

Immunostimulatory nucleic acid (ISS-NA): As used herein, the term immunostimulatory nucleic acid refers to a nucleic acid capable of inducing and/or enhancing an immune response. Immunostimulatory nucleic acids comprise ribonucleic acids and in particular desoxyribonucleic acids, wherein both, ribonucleic acids and desoxyribonucleic acids may be either double stranded or single stranded. Preferred ISS-NA are desoxyribonucleic acids, wherein further preferably said desoxyribonucleic acids are single stranded. Preferably, immunostimulatory nucleic acids contain at least one CpG motif comprising an unmethylated C. Very preferred immunostimulatory nucleic acids comprise at least one CpG motif, wherein said at least one CpG motif comprises or preferably consist of at least one, preferably one, CG dinucleotide, wherein the C is unmethylated. Preferably, but not necessarily, said CG dinucleotide is part of a palindromic sequence. The term immunostimulatory nucleic acid also refers to nucleic acids that contain modified bases, preferably 4-bromo-cytosine. Specifically preferred in the context of the invention are ISS-NA which are capable of stimulating IFN-alpha production in dendritic cells. Immunostimulatory nucleic acids useful for the purpose of the invention are described, for example, in WO2007/068747A1.

Oligonucleotide: As used herein, the term "oligonucleotide" refers to a nucleic acid sequence comprising 2 or more nucleotides, preferably about 6 to about 200 nucleotides, and more preferably 20 to about 100 nucleotides, and most preferably 20 to 40 nucleotides. Very preferably, oligonucleotides comprise about 30 nucleotides, more preferably oligonucleotides comprise exactly 30 nucleotides, and most preferably oligonucleotides consist of exactly 30 nucleotides. Oligonucleotides are polyribonucleotides or polydeoxribonucleotides and are preferably selected from (a) unmodified RNA or DNA, and (b) modified RNA or DNA. The modification may comprise the backbone or nucleotide analogues. Oligonucleotides are preferably selected from the group consisting of (a) single- and double-stranded DNA, (b) DNA that is a mixture of single- and double-stranded regions, (c) single- and double-stranded RNA, (d) RNA that is mixture of single- and double-stranded regions, and (e) hybrid molecules comprising DNA and RNA that are single-stranded or, more preferably, double-stranded or a mixture of single- and double-stranded regions. Preferred nucleotide modifications/analogs are selected from the group consisting of (a) peptide nucleic acid, (b) inosin, (c) tritylated bases, (d) phosphorothioates, (e) alkylphosphorothioates, (f) 5-nitroindole desoxyribofliranosyl, (g) 5-methyldesoxycytosine, and (h) 5,6-dihydro-5,6-dihydroxydesoxythymidine. Phosphothioated nucleotides are protected against degradation in a cell or an organism and are therefore preferred nucleotide modifications. Unmodified oligonucleotides consisting exclusively of phosphodiester bound nucleotides, typically are more active than modified nucleotides and are therefore generally preferred in the context of the invention. Most preferred are oligonucleotides consisting exclusively of phosphodiester bound deoxinucleo tides, wherein further preferably said oligonucleotides are single stranded. Further preferred are oligonucleotides capable of stimulating IFN-alpha production in cells, preferably in dendritic cells. Very preferred oligonucleotides capable of stimulating IFN-alpha production in cells are selected from A-type CpGs and C-type CpGs. Further preferred are RNA-molecules without a Cap.

CpG motif: As used herein, the term "CpG motif refers to a pattern of nucleotides that includes an unmethylated central CpG, i.e. the unmethylated CpG dinucleotide, in which the C is unmethylated, surrounded by at least one base, preferably one or two nucleotides, flanking (on the 3' and the 5' side of) the central CpG. Typically and preferably, the CpG motif as used herein, comprises or alternatively consists of the unmethylated CpG dinucleotide and two nucleotides on its 5' and 3' ends. Without being bound by theory, the bases flanking the CpG confer a significant part of the activity to the CpG oligonucleotide.

Unmethylated CpG-containing oligonucleotide: As used herein, the term "unmethylated CpG-containing oligonucleotide" or "CpG" refers to an oligonucleotide, preferably to an oligodesoxynucleotide, containing at least one CpG motif. Thus, a CpG contains at least one unmethylated cytosine, guanine dinucleotide. Preferred CpGs stimulate/activate, e.g. have a mitogenic effect on, or induce or increase cytokine expression by, a vertebrate bone marrow derived cell. For example, CpGs can be useful in activating B cells, NK cells and antigen-presenting cells, such as dendritic cells, monocytes and macrophages. Preferably, CpG relates to an oligodesoxynucleotide, preferably to a single stranded oligodesoxynucleotide, containing an unmethylated cytosine followed 3' by a guanosine, wherein said unmethylated cytosine and said guanosine are linked by a phosphate bond, wherein preferably said phosphate bound is a phosphodiester bound or a phosphothioate bound, and wherein further preferably said phosphate bond is a phosphodiester bound. CpGs can include nucleotide analogs such as analogs containing phosphorothio ester bonds and can be double-stranded or single-stranded. Generally, double-stranded molecules are more stable in vivo, while single-stranded molecules have increased immune activity. Preferably, as used herein, a CpG is an oligonucleotide that is at least about ten nucleotides in length and comprises at least one CpG motif, wherein further preferably said CpG is 10 to 60, more preferably 15 to 50, still more preferably 20 to 40, still more preferably about 30, and most preferably exactly 30 nucleotides in length. A CpG may consist of methylated and/or unmethylated nucleotides, wherein said at least one CpG motif comprises at least one CG dinucleotide wherein the C is unmethylated. The CpG may also comprise methylated and unmethylated sequence stretches, wherein said at least one CpG motif comprises at least one CG dinucleotide wherein the C is unmethylated. Very preferably, CpG relates to a single stranded oligodesoxynucleotide containing an unmethylated cytosine followed 3' by a guanosine, wherein said unmethylated cytosine and said guanosine are linked by a phosphodiester bound. The CpGs can include nucleotide analogs such as analogs containing phosphorothioester bonds and can be double-stranded or single-stranded. Generally, phosphodiester CpGs are A-type CpGs as indicated below, while phosphothioester stabilized CpGs are B-type CpGs. Preferred CpG oligonucleotides in the context of the invention are A-type CpGs.

A-type CpG: As used herein, the term "A-type CpG" or "D-type CpG" refers to an oligodesoxynucleotide (ODN) comprising at least one CpG motif. A-type CpGs preferentially stimulate activation of T cells and the maturation of dendritic cells and are capable of stimulating IFN-alpha production. In A-type CpGs, the nucleotides of the at least one CpG motif are linked by at least one phosphodiester bond. A-type CpGs comprise at least one phosphodiester bond CpG motif which may be flanked at its 5' end and/or, preferably and, at its 3' end by phosphorothioate bound nucleotides. Preferably, the CpG motif, and hereby preferably the CG dinucleotide and its immediate flanking regions comprising at least one, preferably two nucleotides, are composed of phosphodiester nucleotides. Preferred A-type CpGs exclusively consist of phosphodiester (PO) bond nucleotides. Typically and preferably, the poly G motif comprises or alternatively consists of at least one, preferably at least three, at least 4, 5, 6, 7, 8, 9, 10, 11, 12, 13, 14, or 15 Gs (guanosines), most preferably by at least 10 Gs. Preferably, the A-type CpG of the invention comprises or alternatively consists of a palindromic sequence.

Packaged: The term "packaged" as used herein refers to the state of a polyanionic macromolecule or immunostimulatory substances in relation to the core particle and VLP, respectively. The term "packaged" as used herein includes binding that may be covalent, e.g., by chemically coupling, or non-covalent, e.g., ionic interactions, hydrophobic interactions, hydrogen bonds, etc. The term also includes the enclosement, or partial enclosement, of a polyanionic macromolecule. Thus, the polyanionic macromolecule or immunostimulatory substances can be enclosed by the VLP without the existence of an actual binding, in particular of a covalent binding. In preferred embodiments, the at least one polyanionic macromolecule or immunostimulatory substances is packaged inside the VLP, most preferably in a non-covalent manner. In case said immunostimulatory substances is nucleic acid, preferably a DNA, the term packaged implies that said nucleic acid is not accessible to nucleases hydrolysis, preferably not accessible to DNAse hydrolysis (e.g. DNaseI or Benzonase), wherein preferably said accessibility is assayed as described in Examples 11-17 of WO2003/024481A2.

Thus, in a first aspect, the present invention provides for a composition for use in a method of preventing or treating canine atopic dermatitis (CAD) of a canidae, preferably of a domestic dog, wherein an effective amount of said composition is administered to said canidae, preferably to said domestic dog, and wherein said composition comprises (a) a core particle with at least one first attachment site; and (b) at least one canine Interleukin-31 antigen (cIL-31 antigen) with at least one second attachment site, wherein said cIL-31 antigen comprises, or preferably consists of, a protein with the amino sequence selected from SEQ ID NO:22 or a protein with an amino acid sequence of at least 90%, preferably of at least 92%, further preferably of at least 95%, and again further preferably of at least 98% amino acid sequence identity with SEQ ID NO:22; wherein (a) and (b) are linked through said at least one first and said at least one second attachment site via at least one non-peptide covalent bond.

In a preferred embodiment, said core particle is a virus-like particle (VLP), preferably a recombinant VLP. In a further preferred embodiment, said VLP is a modified VLP of cucumber mosaic virus (CMV), wherein said modified VLP of CMV comprises, essentially consists of, or alternatively consists of, at least one modified CMV polypeptide, wherein said modified CMV polypeptide comprises, or preferably consists of, (a) a CMV polypeptide, and (b) a T helper cell epitope; and wherein said CMV polypeptide comprises, or preferably consists of, (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%. In a further very preferred embodiment, said CMV polypeptide comprises, or preferably consists of, (a) an amino acid sequence of a coat protein of CMV, wherein said amino acid sequence comprises, or preferably consists of, SEQ ID NO:1 or (b) an amino acid sequence having a sequence identity of at least 90% of SEQ ID NO:1; and wherein said amino sequence as defined in (a) or (b) in this claim comprises SEQ ID NO:23; or wherein said amino sequence as defined in (a) or (b) in this claim comprises an amino acid sequence region, wherein said amino acid sequence region has a sequence identity of at least 90% with SEQ ID NO:23. In a further very preferred embodiment, said VLP is a modified VLP of cucumber mosaic virus (CMV), wherein said modified CMV polypeptide comprises, preferably consists of, an amino acid sequence of SEQ ID NO:6 or SEQ ID NO:7.

In a further very preferred embodiment, said at least one cIL-31 antigen comprises, or preferably consists of, a protein with the amino sequence selected from: (a) SEQ ID NO:18; (b) SEQ ID NO:21; (c) SEQ ID NO:22; (d) SEQ ID NOs:25-30. In a further very preferred embodiment, said at least one cIL-31 antigen comprises, or preferably consists of, a protein with the amino sequence selected from: (a) SEQ ID NO:18; (b) SEQ ID NO:21; (c) SEQ ID NO:22; (d) SEQ ID NO:25; or (e) SEQ ID NO:26. In a further very preferred embodiment, said second attachment site is a sufhydryl group, and wherein preferably said sulfhydryl group is derived from reaction of said cIL-31 antigen with N-succinimidyl S-acetylthioacetate (SATA). In a further very preferred embodiment, said second attachment site is a sulfhydryl group, and wherein preferably said sulfhydryl group is derived from reaction of a lysine residue of said cIL-31 antigen.

In another aspect, the present invention provides for the present invention provides for a composition for use in a method of preventing or treating canine atopic dermatitis (CAD) of a domestic dog, wherein an effective amount of said composition is administered to said domestic dog, and wherein said composition comprises (a) a core particle with at least one first attachment site, wherein said core particle is preferably a virus-like particle (VLP), further preferably a recombinant VLP; and (b) at least one canine Interleukin-31 antigen (cIL-31 antigen) with at least one second attachment site, wherein said cIL-31 antigen comprises, or preferably consists of, a protein with the amino sequence selected from SEQ ID NO:22 or a protein with an amino acid sequence of at least 90%, preferably of at least 92%, further preferably of at least 95%, and again further preferably of at least 98% amino acid sequence identity with SEQ ID NO:22; wherein (a) and (b) are linked through said at least one first and said at least one second attachment site via at least one non-peptide covalent bond.

In a preferred embodiment, said virus-like particle (VLP) is derived from a plant virus. In another preferred embodiment, said VLP is a recombinant VLP, and wherein preferably said recombinant VLP is derived from a plant virus. In another preferred embodiment, said VLP is a VLP of cucumber mosaic virus (CMV).

In a preferred embodiment, said VLP is a modified VLP comprising, essentially consisting of, or alternatively consisting of, at least one modified VLP polypeptide, wherein said modified VLP polypeptide comprises, or preferably consists of, (a) a VLP polypeptide, and (b) a T helper cell epitope, wherein said VLP polypeptide comprises, or preferably consists of, (i) an amino acid sequence of a coat protein of a virus, preferably an amino acid sequence of a coat protein of a plant virus; or (ii) a mutated amino acid sequence, wherein the amino acid sequence to be mutated is an amino acid sequence of said coat protein of a virus, and wherein said mutated amino acid sequence and said coat protein of a virus show a sequence identity of at least 90%, preferably of at least 95%, further preferably of at least 98% and again more preferably of at least 99%.

In a preferred embodiment, said VLP is a modified VLP of cucumber mosaic virus (CMV), wherein said modified VLP of CMV comprises, essentially consists of, or alternatively consists of, at least one modified CMV polypeptide, wherein said modified CMV polypeptide comprises, or preferably consists of, (a) a CMV polypeptide, and (b) a T helper cell epitope; and wherein said CMV polypeptide comprises, or preferably consists of, (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%.

In a preferred embodiment, said CMV polypeptide comprises, preferably consists of, an amino acid sequence of a coat protein of CMV. In another preferred embodiment, said CMV polypeptide comprises, preferably consists of a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%. Typically and preferably, said mutated amino acid sequence and said amino acid sequence to be mutated differ in least one and in at most 11, 10, 9, 8, 7, 6, 5, 4, 3, or 2 amino acid residues, and wherein preferably these differences are selected from (i) insertion, (ii) deletion, (iii) amino acid exchange, and (iv) any combination of (i) to (iii).

In another preferred embodiment, said CMV polypeptide comprises, or preferably consists of, (i) (a) an amino acid sequence of a coat protein of CMV, wherein said amino acid sequence comprises, or preferably consists of, SEQ ID NO:1 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 95%, preferably of at least 98%, and more preferably of at least 99%.

In another preferred embodiment, said CMV polypeptide comprises, or preferably consists of, (a) an amino acid sequence of a coat protein of CMV, wherein said amino acid sequence comprises, or preferably consists of, SEQ ID NO:1 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1.

In another preferred embodiment, said CMV polypeptide comprises, or preferably consists of, (i) (a) an amino acid sequence of a coat protein of CMV, wherein said amino acid sequence comprises SEQ ID NO:23, or (b) an amino acid sequence of a coat protein of CMV comprising an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:23; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 95%, preferably of at least 98%, and more preferably of at least 99%.

In a further preferred embodiment, said CMV polypeptide comprises, or preferably consists of, (a) an amino acid sequence of a coat protein of CMV, wherein said amino acid sequence comprises SEQ ID NO:23, or (b) an amino acid sequence of a coat protein of CMV comprising an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:23.

In another preferred embodiment, said CMV polypeptide comprises, or preferably consists of, (i) (a) an amino acid sequence of a coat protein of CMV, wherein said amino acid sequence comprises, or preferably consists of, SEQ ID NO:1 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1; and wherein said amino sequence as defined in (a) or (b) in this claim comprises SEQ ID NO:23; or wherein said amino sequence as defined in (a) or (b) in this claim comprises an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:23; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 98% preferably of at least 99%.

In another preferred embodiment, said CMV polypeptide comprises, or preferably consists of, (a) an amino acid sequence of a coat protein of CMV, wherein said amino acid sequence comprises, or preferably consists of, SEQ ID NO:1 or (b) an amino acid sequence having a sequence identity of at least 90% of SEQ ID NO:1; and wherein said amino sequence as defined in (a) or (b) in this claim comprises SEQ ID NO:23; or wherein said amino sequence as defined in (a) or (b) in this claim comprises an amino acid sequence region, wherein said amino acid sequence region has a sequence identity of at least 90% with SEQ ID NO:23.

In another preferred embodiment, said T helper cell epitope replaces a N-terminal region of said CMV polypeptide. In another preferred embodiment the number of amino acids of said N-terminal region replaced is equal to or lower than the number of amino acids of which said T helper cell epitope consists.

In a further very preferred embodiment, said T helper cell epitope replaces a N-terminal region of said CMV polypeptide, and wherein the number of amino acids of said N-terminal region replaced is equal to or lower than the number of amino acids of which said T helper cell epitope consists. Typically and preferably, said replaced N-terminal region of said CMV polypeptide consists of 5 to 15 consecutive amino acids, preferably of 9 to 14 consecutive amino acids, more preferably of 11 to 13 consecutive amino acids.

In a further very preferred embodiment, said N-terminal region of said CMV polypeptide corresponds to amino acids 2-12 of SEQ ID NO:1.

In another very preferred embodiment, said T helper cell epitope is a universal T helper cell epitope. In another preferred embodiment, said T helper cell epitope consists of at most 20 amino acids.

In a very preferred embodiment, said Th cell epitope is a PADRE sequence. In a further very referred embodiment, said Th cell epitope comprises, preferably consists of, the amino acid sequence of SEQ ID NO:5. In another very preferred embodiment, said Th cell epitope is a PADRE sequence, and wherein said Th cell epitope comprises, preferably consists of, the amino acid sequence of SEQ ID NO:5.

In another preferred embodiment, said T helper cell epitope is derived from a human vaccine. In a very preferred embodiment, said Th cell epitope is derived from tetanus toxin. In a further very referred embodiment, said Th cell epitope has, preferably consists of, the amino acid sequence of SEQ ID NO:4. In another very preferred embodiment, said Th cell epitope is derived from tetanus toxin, and wherein said Th cell epitope has, preferably consists of, the amino acid sequence of SEQ ID NO:4.

In a very preferred embodiment, said Th cell epitope is a PADRE sequence, and wherein said Th cell epitope comprises, preferably consists of, the amino acid sequence of SEQ ID NO:5; or wherein said Th cell epitope is derived from tetanus toxin, and wherein said Th cell epitope has, preferably consists of, the amino acid sequence of SEQ ID NO:4.

In a very preferred embodiment, said CMV polypeptide comprises, or preferably consists of, an amino acid sequence of a coat protein of CMV, wherein said amino acid sequence comprises, or preferably consists of, SEQ ID NO:1 or an amino acid sequence having a sequence identity of at least 95% of SEQ ID NO:1; and wherein said amino sequence comprises SEQ ID NO:23, and wherein said T helper cell epitope replaces the N-terminal region of said CMV polypeptide, and wherein said replaced N-terminal region of said CMV polypeptide consists of 11 to 13 consecutive amino acids, preferably of 11 consecutive amino acids, and wherein further preferably said N-terminal region of said CMV polypeptide corresponds to amino acids 2-12 of SEQ ID NO:1.

In another very preferred embodiment, said modified CMV polypeptide comprises, preferably consists of, an amino acid sequence of SEQ ID NO:6. In another very preferred embodiment, said modified CMV polypeptide comprises, preferably consists of, an amino acid sequence of SEQ ID NO:7. The use of a composition of any one of the claims 6 to 8, wherein said modified CMV polypeptide comprises, preferably consists of, an amino acid sequence of SEQ ID NO:6 or SEQ ID NO:7.

In a very preferred embodiment, said first attachment site and said second attachment site are linked via at least one covalent non-peptide-bond. In another very preferred embodiment, said first attachment site comprises, or preferably is, an amino group, preferably an amino group of a lysine. In a further very preferred embodiment, said second attachment site comprises, or preferably is, a sulfhydryl group, preferably a sulfhydryl group of a cysteine.

In a very preferred embodiment, the at least one first attachment site is an amino group, preferably an amino group of a lysine residue and the at least one second attachment site is a sulfhydryl group, preferably a sulfhydryl group of a cysteine residue or a sufhydryl group that has been chemically attached to the cIL-31 antigen. In a further preferred embodiment only one of said second attachment sites associates with said first attachment site through at least one non-peptide covalent bond leading to a single and uniform type of binding of said cIL-31 antigen to said modified virus-like particle, wherein said only one second attachment site that associates with said first attachment site is a sulfhydryl group, and wherein said cIL-31 antigen and said modified virus-like particle interact through said association to form an ordered and repetitive antigen array, i.e. an ordered and repetitive array of cIL-31 antigens.

In one preferred embodiment of the invention, the cIL-31 antigen is linked to the modified VLP by way of chemical cross-linking, typically and preferably by using a heterobifunctional cross-linker. In preferred embodiments, the hetero-bifunctional cross-linker contains a functional group which can react with the preferred first attachment sites, preferably with the amino group, more preferably with the amino groups of lysine residue(s) of the modified VLP, and a further functional group which can react with the preferred second attachment site, i.e. a sulfhydryl group, preferably of cysteine(s) residue inherent of, or artificially added to the cIL-31 antigen, and optionally also made available for reaction by reduction. Several hetero-bifunctional cross-linkers are known to the art. These include the preferred cross-linkers SMPH (Pierce), Sulfo-MBS, Sulfo-EMCS, Sulfo-GMBS, Sulfo-SIAB, Sulfo-SMPB, Sulfo-SMCC, Sulfo-KMUS SVSB, SIA, and other cross-linkers available for example from the Pierce Chemical Company, and having one functional group reactive towards amino groups and one functional group reactive towards sulfhydryl groups. The above mentioned cross-linkers all lead to formation of an amide bond after reaction with the amino group and a thioether linkage with the sulfhydryl groups. Another class of cross-linkers suitable in the practice of the invention is characterized by the introduction of a disulfide linkage between the cIL-31 antigen and the modified VLP upon coupling. Preferred cross-linkers belonging to this class include, for example, SPDP and Sulfo-LC-SPDP (Pierce). In a very preferred embodiment, said hetero-bifunctional cross-linker is SMPH.

Linking of the cIL-31 antigen to the modified VLP by using a hetero-bifunctional cross-linker according to the preferred methods described above, allows coupling of the cIL-31 antigen to the modified VLP in an oriented fashion. Other methods of linking the cIL-31 antigen to the modified VLP include methods wherein the cIL-31 antigen is cross-linked to the modified VLP, using the carbodiimide EDC, and NHS. The cIL-31 antigen may also be first thiolated through reaction, for example with SATA, SATP or iminothiolane. The cIL-31 antigen, after deprotection if required, may then be coupled to the modified VLP as follows. After separation of the excess thiolation reagent, the cIL-31 antigen is reacted with the modified VLP, previously activated with a hetero-bifunctional cross-linker comprising a cysteine reactive moiety, and therefore displaying at least one or several functional groups reactive towards cysteine residues, to which the thiolated cIL-31 antigen can react, such as described above. Optionally, low amounts of a reducing agent are included in the reaction mixture. In further methods, the cIL-31 antigen is attached to the modified VLP, using a homo-bifunctional cross-linker such as glutaraldehyde, DSG, BM[PEO]4, BS3, (Pierce) or other known homo-bifunctional cross-linkers with functional groups reactive towards amine groups or carboxyl groups of the modified VLP.

In a further preferred embodiment said composition further comprises at least one immuno-stimulatory substance. In a very preferred embodiment, said immunostimulatory substance is packaged into the modified VLPs of the invention. In another preferred embodiment, the immunostimulatory substance is mixed with the modified VLPs of the invention. Immunostimulatory substances useful for the invention are generally known in the art and are disclosed, inter alia, in WO2003/024481A2.

In another embodiment of the present invention, said immunostimulatory substance consists of DNA or RNA of non-eukaryotic origin. In a further preferred embodiment said immunostimulatory substance is selected from the group consisting of: (a) immunostimulatory nucleic acid; (b) peptidoglycan; (c) lipopolysaccharide; (d) lipoteichonic acid; (e) imidazoquinoline compound; (f) flagelline; (g) lipoprotein; and (h) any mixtures of at least one substance of (a) to (g). In a further preferred embodiment said immunostimulatory substance is an immunostimulatory nucleic acid, wherein said immunostimulatory nucleic acid is selected from the group consisting of: (a) ribonucleic acids; (b) deoxyribonucleic acids; (c) chimeric nucleic acids; and (d) any mixture of (a), (b) and/or (c). In a further preferred embodiment said immunostimulatory nucleic acid is a ribonucleic acid, and wherein said ribonucleic acid is bacteria derived RNA. In a further preferred embodiment said immunostimulatory nucleic is poly-(I.C) or a derivative thereof. In a further preferred embodiment said immunostimulatory nucleic acid is a deoxyribonucleic acid, wherein said deoxyribonucleic acid is an unmethylated CpG-containing oligonucleotide.

In a very preferred embodiment said immunostimulatory substance is an unmethylated CpG-containing oligonucleotide. In a further preferred embodiment said unmethylated CpG-containing oligonucleotide is an A-type CpG. In a further preferred embodiment said A-type CpG comprises the sequence GACGATCGTC (SEQ ID NO:24). In a further preferred embodiment said palindromic sequence is flanked at its 5'-terminus and at its 3'-terminus by guanosine entities. In a further preferred embodiment said palindromic sequence is flanked at its 5'-terminus by at least 3 and at most 15 guanosine entities, and wherein said palindromic sequence is flanked at its 3'-terminus by at least 3 and at most 15 guanosine entities.

In another preferred embodiment, said immunostimulatory substance is an unmethylated CpG-containing oligonucleotide, and wherein preferably said unmethylated CpG-containing oligonucleotide comprises a palindromic sequence, and wherein further preferably the CpG motif of said unmethylated CpG-containing oligonucleotide is part of a palindromic sequence, and wherein again further preferably said palindromic sequence is GACGATCGTC (SEQ ID NO:24).

In very preferred embodiments, said at least one cIL-31 antigen is linked via a sulfhydryl group to said core particle, preferably to said VLP, again further preferably to said modified CMV VLP, wherein preferably said sulfhydryl group is comprised by said second attachment site and wherein said sulfhydryl group is not naturally occurring with said cIL-31 antigen, and wherein preferably said sulfhydryl group is derived from reaction of said cIL-31 antigen with N-succinimidyl S-acetylthioacetate (SATA), N-succinimidyl S-acetylthiopropionate (SATP) or iminothiolane, further preferably wherein said sulfhydryl group is derived from reaction of said cIL-31 antigen with N-succinimidyl S-acetylthioacetate (SATA). In a further very preferred embodiment, said second attachment site is a sulfhydryl group, and wherein preferably said sulfhydryl group is derived from reaction of a lysine residue of said cIL-31 antigen.

In other preferred embodiments of the invention, the cIL-31 antigen is linked via a cysteine residue, having been added to either the N-terminus or the C-terminus of, or a natural cysteine residue within the cIL-31 antigen, to lysine residues of the modified virus-like particle. In a preferred embodiment, the composition of the invention further comprises a linker, wherein said linker associates said cIL-31 antigen with said second attachment site, and wherein preferably said linker comprises or alternatively consists of said second attachment site.

In a preferred embodiment, said cIL-31 antigen comprises, or preferably consists of, a protein with an amino acid sequence of at least 90%, amino acid sequence identity with SEQ ID NO:22. In another preferred embodiment, said cIL-31 antigen comprises, or preferably consists of, a protein with an amino acid sequence of at least 92%, amino acid sequence identity with SEQ ID NO:22. In a further preferred embodiment, said cIL-31 antigen comprises, or preferably consists of, a protein with an amino acid sequence of at least 95%, amino acid sequence identity with SEQ ID NO:22. In a very preferred embodiment, said cIL-31 antigen comprises, or preferably consists of, a protein with an amino acid sequence of at least 98%, amino acid sequence identity with SEQ ID NO:22. In a further very preferred embodiment, said cIL-31 antigen comprises, or preferably consists of, a protein with an amino acid sequence of SEQ ID NO:22. In a further very preferred embodiment, said at least one cIL-31 antigen comprises, or preferably consists of, a protein with the amino sequence of SEQ ID NO:18. In a further very preferred embodiment, said at least one cIL-31 antigen comprises, or preferably consists of, a protein with the amino sequence of SEQ ID NO:21. In a further very preferred embodiment, said second attachment site is a sulfhydryl group, and wherein preferably said sulfhydryl group is derived from reaction of said cIL-31 antigen with N-succinimidyl S-acetylthioacetate (SATA). In a further very preferred embodiment, said second attachment site is a sulfhydryl group, and wherein preferably said sulfhydryl group is derived from reaction of a lysine residue of said cIL-31 antigen.

In a further aspect, the present invention provides for a composition comprising (a) a virus-like particle (VLP) with at least one first attachment site; (b) at least one canine Interleukin-31 antigen (cIL-31 antigen) with at least one second attachment site, wherein said cIL-31 antigen comprises, or preferably consists of, a protein with the amino sequence selected from SEQ ID NO:22 or a protein with an amino acid sequence of at least 90%, preferably of at least 92%, further preferably of at least 95%, and again further preferably of at least 98% amino acid sequence identity with SEQ ID NO:22, and again further preferably said antigen comprises, or preferably consists of a protein with the amino sequence of SEQ ID NO:22; wherein (a) and (b) are linked through said at least one first and said at least one second attachment site via at least one non-peptide covalent bond.

In a further very preferred embodiment, said VLP is a modified VLP of cucumber mosaic virus (CMV), wherein said modified CMV polypeptide comprises, preferably consists of, an amino acid sequence of SEQ ID NO:6 or SEQ ID NO:7.

In a further very preferred embodiment, said at least one cIL-31 antigen comprises, or preferably consists of, a protein with the amino sequence selected from: (a) SEQ ID NO:18; (b) SEQ ID NO:21; (c) SEQ ID NO:22; (d) SEQ ID NOs:25-30. In a further very preferred embodiment, said at least one cIL-31 antigen comprises, or preferably consists of, a protein with the amino sequence selected from: (a) SEQ ID NO:18; (b) SEQ ID NO:21; (c) SEQ ID NO:22; (d) SEQ ID NO:25; or (e) SEQ ID NO:26. In a further preferred embodiment, said cIL-31 antigen comprises, or preferably consists of, a protein with an amino acid sequence of at least 95%, amino acid sequence identity with SEQ ID NO:22. In a very preferred embodiment, said cIL-31 antigen comprises, or preferably consists of, a protein with an amino acid sequence of at least 98%, amino acid sequence identity with SEQ ID NO:22. In a further very preferred embodiment, said cIL-31 antigen comprises, or preferably consists of, a protein with an amino acid sequence of SEQ ID NO:22. In a further very preferred embodiment, said at least one cIL-31 antigen comprises, or preferably consists of, a protein with the amino sequence of SEQ ID NO:18. In a further very preferred embodiment, said at least one cIL-31 antigen comprises, or preferably consists of, a protein with the amino sequence of SEQ ID NO:21. In a further very preferred embodiment, said second attachment site is a sulfhydryl group, and wherein preferably said sulfhydryl group is derived from reaction of said cIL-31 antigen with N-succinimidyl S-acetylthioacetate (SATA). In a further very preferred embodiment, said second attachment site is a sulfhydryl group, and wherein preferably said sulfhydryl group is derived from reaction of a lysine residue of said cIL-31 antigen.

In another aspect, the present invention provides for a method of preventing or treating canine atopic dermatitis (CAD) of a canidae, preferably of a domestic dog, comprising administering an effective amount of a composition to said canidae, preferably to said domestic dog, and wherein said composition comprises (a) a core particle with at least one first attachment site; and (b) at least one canine Interleukin-31 antigen (cIL-31 antigen) with at least one second attachment site, wherein said cIL-31 antigen comprises, or preferably consists of, a protein with the amino sequence selected from SEQ ID NO:22 or a protein with an amino acid sequence of at least 90%, preferably of at least 92%, further preferably of at least 95%, and again further preferably of at least 98% amino acid sequence identity with SEQ ID NO:22; wherein (a) and (b) are linked through said at least one first and said at least one second attachment site via at least one non-peptide covalent bond, wherein preferably said method or said composition is further defined as described herein.

In another aspect, the present invention provides for a use of a composition comprising (a) a core particle with at least one first attachment site; and (b) at least one canine Interleukin-31 antigen (cIL-31 antigen) with at least one second attachment site, wherein said cIL-31 antigen comprises, or preferably consists of, a protein with the amino sequence selected from SEQ ID NO:22 or a protein with an amino acid sequence of at least 90%, preferably of at least 92%, further preferably of at least 95%, and again further preferably of at least 98% amino acid sequence identity with SEQ ID NO:22; wherein (a) and (b) are linked through said at least one first and said at least one second attachment site via at least one non-peptide covalent bond; for the manufacture of a medicament for preventing or treating canine atopic dermatitis (CAD) of a canidae, preferably of a domestic dog, wherein an effective amount of said composition is administered to said canidae, preferably to said domestic dog, and wherein preferably said method or said composition is further defined as described herein.

EXAMPLES

Example 1

Isolation and Cloning of a Coat Protein (CP) of Cucumber Mosaic Virus (CMV)

Total RNA from CMV-infected lily leaves was isolated using TRI reagent (Sigma, Saint Louis, USA) in accordance with manufacturer's instructions. For cDNA synthesis, a OneStep RT-PCR kit (Qiagen, Venlo, Netherlands) was used. For amplification of the CMV CP gene, primer sequences were chosen following analysis of CMV sequences from GenBank: CMcpF (CA CCATGGACAAATCTGAATCAACCAGTGCTGGT) (SEQ ID NO:8) and CMcpR (CA AAGCTTATCAAACTGGGAGCACCCCAGATGTGGGA) (SEQ ID NO:9); NcoI and HindIII sites are underlined. The corresponding PCR products were cloned into the pTZ57R/T vector (Fermentas, Vilnius, Lithuania). *E. coli* XL1-Blue cells were used as a host for cloning and plasmid amplification. To avoid selecting clones containing PCR errors, several CP gene-containing pTZ57 plasmid clones were sequenced using a BigDye cycle sequencing kit and an ABI Prism 3100 Genetic analyzer (Applied Biosystems, Carlsbad, USA). After sequencing, a cDNA of the CMV CP gene without sequence errors (SEQ ID NO:10) coding for CMV coat protein of SEQ ID NO:1 was then subcloned into the NcoI/HindIII sites of the pET28a(+) expression vector (Novagen, San Diego, USA), resulting in the expression plasmid pET-CMVwt (FIG. 1).

Example 2

Expression of CP of SEQ ID NO:1 in *E. coli* Leading to VLPs of CMV

To obtain CMV VLPs, *E. coli* C2566 cells (New England Biolabs, Ipswich, USA) were transformed with the CMV CP gene-containing plasmid pET-CMVwt. After selection of clones with the highest expression levels of target protein, *E. coli* cultures were grown in 2×TY medium containing kanamycin (25 mg/l) on a rotary shaker (200 rev/min; Infors, Bottmingen, Switzerland) at 30° C. to an OD600 of 0.8-1.0. Then, the cells were induced with 0.2 mM IPTG, and the medium was supplemented with 5 mM MgCl2. Incubation was continued on the rotary shaker at 20° C. for 18 h. The resulting biomass was collected by low-speed centrifugation and was frozen at −20° C. After thawing on ice, the cells were suspended in the buffer containing 50 mM sodium citrate, 5 mM sodium borate, 5 mM EDTA, 5 mM mercaptoethanol (pH 9.0, buffer A) and were disrupted by ultrasonic treatment. Insoluble proteins and cell debris were removed by centrifugation (13,000 rpm, 30 min at 5° C.). The soluble CMV CP protein in clarified lysate was pelleted using saturated ammonium sulfate (1:1, vol/vol) overnight at +4° C. Precipitated proteins were solubilized in the same buffer A (without mercaptoethanol) for 4 h at +4° C. Insoluble proteins were removed by low speed centrifugation (13,000 rpm, 15 min at 4° C.). Soluble CMV CP-containing protein solution was separated from the cellular proteins by ultracentrifugation (SW28 rotor, Beckman, Palo Alto, USA; at 25,000 rpm, 6 h, 5° C.) in a sucrose gradient (20-60% sucrose in buffer A, without mercaptoethanol, supplemented with 0.5% Triton X-100). The gradient was divided into six fractions, starting at the bottom of the gradient, and the fractions were analyzed by SDS-PAGE (data not shown). Fractions No. 2 and No. 3 containing recombinant CMV CP were combined and were dialyzed against 200 volumes of the buffer (5 mM sodium borate, 2 mM EDTA, pH 9.0) to remove the sucrose and Triton X-100. After dialysis, CMV CP solution was sterilized by filtration through the 0.2μ filter. Next, CMV CP was concentrated using Type70 rotor (Beckman, Palo Alto, USA) ultracentrifugation through the 20% sucrose "cushion" under sterile conditions (50 000 rpm, 4 h, +5° C.). The concentration of purified CMVwt was estimated using the QuBit fluorometer in accordance with manufacturer's recommendations (Invitrogen, Eugene, USA). Concentrated VLP solutions (approx. 3 mg/ml) were stored at +4° C. in 5 mM sodium borate, 2 mM EDTA, buffer (pH 9.0). All steps involved in the expression and purification of VLP were monitored by SDS-PAGE using 12.5% gels.

Figure 2A:
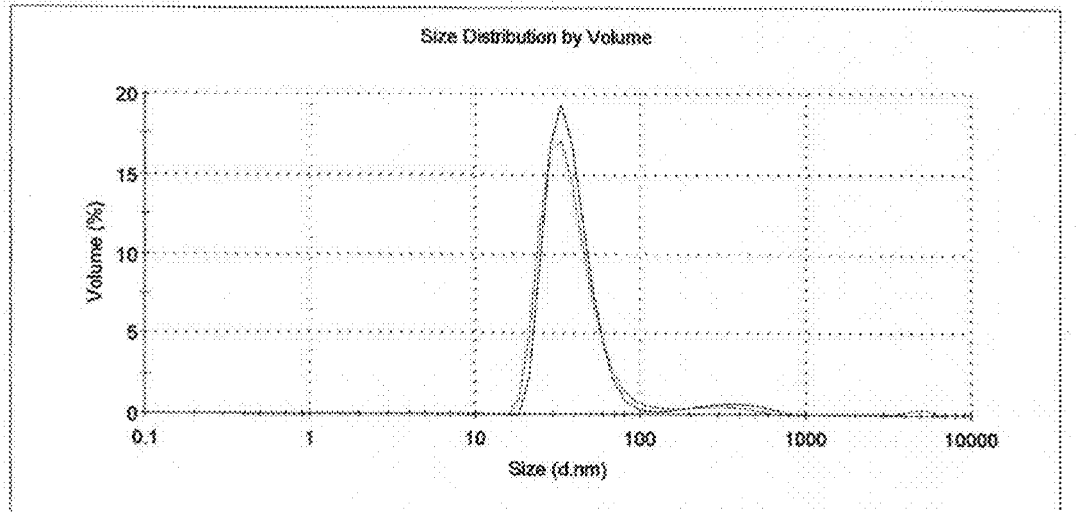
FIG. 2A Dynamic light scattering of purified CMVwt VLPs. The size of particles was detected by using Zetasizer Nano ZS (Malvern Instruments Ltd., United Kingdom).
Figure 2B:
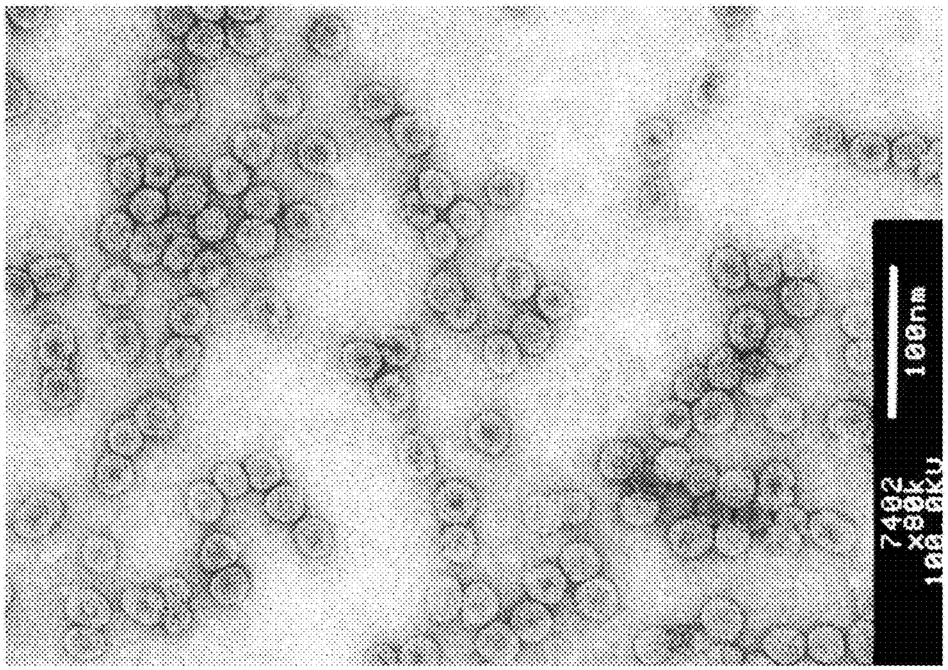
FIG. 2B Electron-microscopy analysis of purified CMVwt VLPs. For the morphological analysis of VLPs the JEM-1230 electron microscope (Jeol Ltd., Tokyo, Japan) was used.

CMV coat protein can be successfully expressed in *E. coli* cells and significant part obtained can be in soluble fraction. Moreover, these proteins are found directly in *E. coli* cell extracts in the form of isometric VLPs, as demonstrated by sucrose gradient analysis (FIG. 2A), dynamic light scattering and electron-microscopy analysis (FIG. 2B).

Example 3

Cloning of a Modified Coat Protein of CMV Containing a Tetanus Toxoid Epitope (CMV-Ntt830)

To replace the original amino acids at the N-terminus of CMV CP of SEQ ID NO:1 with the tetanus toxoid epitope coding sequence, the pET-CMVwt plasmid was used for PCR amplification and mutagenesis. A SalI site located within the CMVwt gene (FIG. 1) was used for cloning the corresponding PCR products.

To introduce the tetanus toxoid epitope coding sequence into the CMVwt gene, a two step PCR mutagenesis was used. For the first step amplification, the following primers were used: pET-220 (AGCACCGCCGCCGCAAGGAA (SEQ ID NO:11)—upstream from polylinker, the amplified region includes BglII site) and CMV-tt83-1R (ATTTGGAGTTGGCCTTAATATACTGGCC-CATGGTATATCTCCTTCTTAAAGT) (SEQ ID NO:12). For the second round, the PCR product from the first amplification was diluted 1:50 and re-amplified with primers pET-220 (SEQ ID NO: 11) and CMV-tt83Sal-R2 (GACGTCGACGCTCGGTAATCCCGATAAATTTG-GAGTTGGCCTTAATATACTG) (SEQ ID NO:13). The resulting PCR product (cDNA of SEQ ID NO:14 coding for CMV-Ntt830 of SEQ ID NO:6) was subcloned in BglII/SaLI sites of pET-CMVwt. The correct clone was identified by sequencing and designated pET-CMV-Ntt830.

Example 4

Expression of CMV-Ntt830 in *E. coli* Leading to Modified VLPs of CMV

Figure 3A:
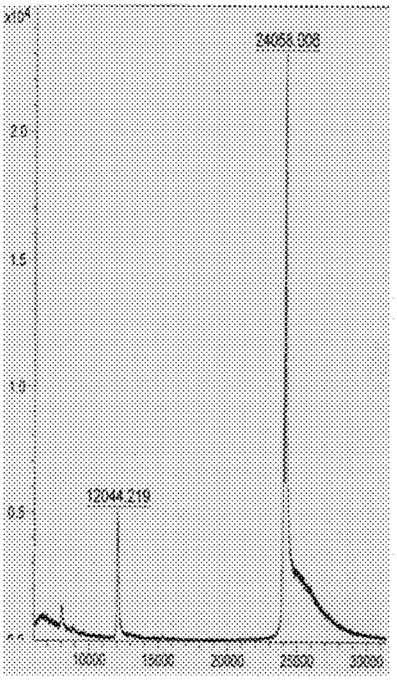
FIG. 3A CMVwild-type ("wt"); theoretical MM=24069; found MM=24058
Figure 3B:
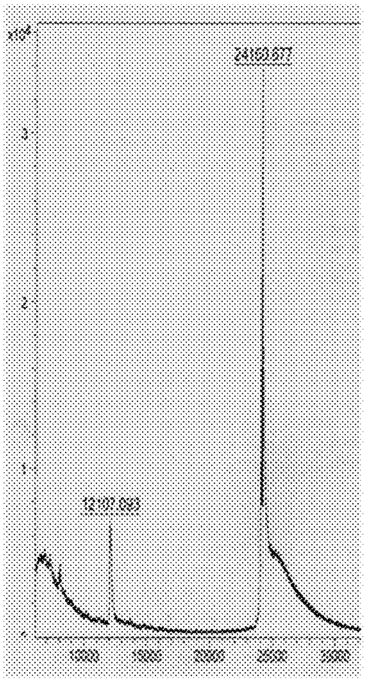
FIG. 3B CMV-Npadr; theoretical MM=24161 (without first Met); found MM=24160
Figure 3C:
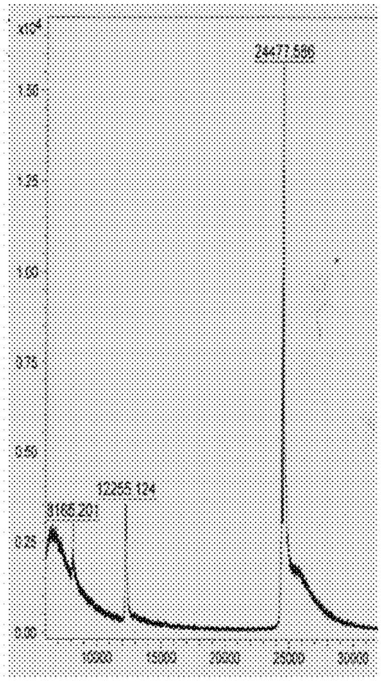
FIG. 3C CMV-Ntt830; theoretical MM=24483 (without first Met); found MM=24477
Figure 4A:
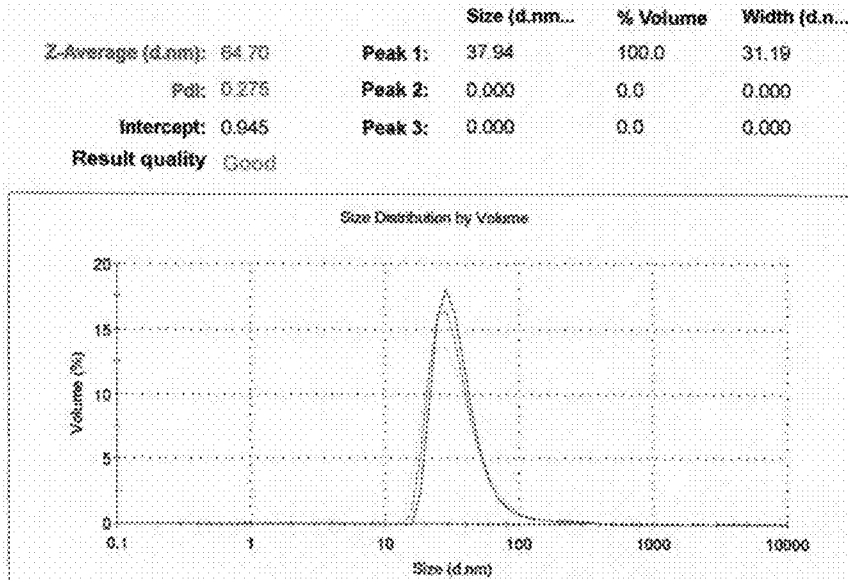
FIG. 4A Dynamic light scattering of purified CMV-Ntt830 VLPs. The size of particles was detected by using Zetasizer Nano ZS (Malvern Instruments Ltd., United Kingdom).
Figure 4B:
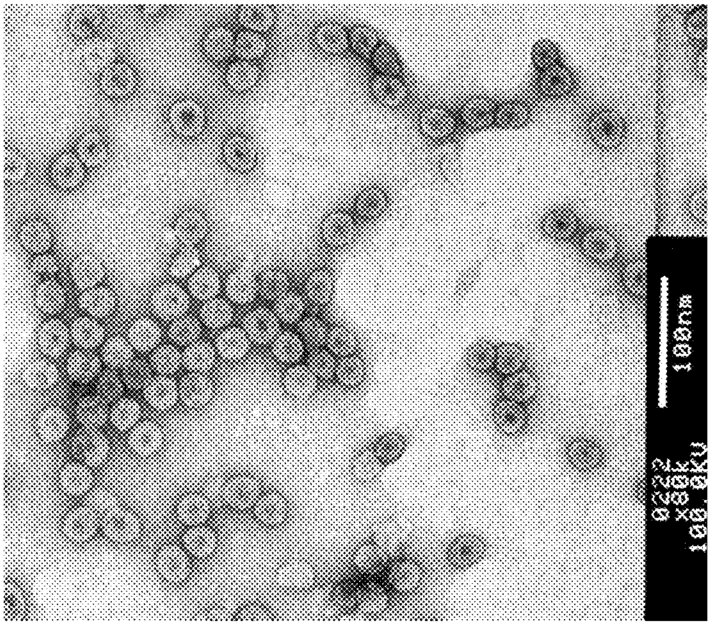
FIG. 4B Electron-microscopy analysis of purified CMV-Ntt830 VLPs. For the morphological analysis of VLPs the JEM-1230 electron microscope (Jeol Ltd., Tokyo, Japan) was used.

To obtain CMV-Ntt830 VLPs, *E. coli* C2566 cells (New England Biolabs, Ipswich, USA) were transformed with the CMV-Ntt830 gene-containing plasmid pET-CMV-Ntt830. After selection of clones with the highest expression levels of target protein, *E. coli* cultures were grown in 2×TY medium containing kanamycin (25 mg/l) in a rotary shaker (200 rev/min; Infors, Bottmingen, Switzerland) at 30° C. to an OD600 of 0.8-1.0. The, cells were then induced with 0.2 mM IPTG, and the medium supplemented with 5 mM $MgCl_2$. Incubation was continued on the rotary shaker at 20° C. for 18 h. The resulting biomass was collected by low-speed centrifugation and frozen at −20° C. After thawing on ice, the cells were suspended in buffer containing 50 mM sodium citrate, 5 mM sodium borate, 5 mM EDTA, 5 mM mercaptoethanol (pH 9.0, buffer A) and disrupted by sonication. Insoluble proteins and cell debris were removed by centrifugation (13,000 rpm, 30 min at 5° C.). The soluble CMV-Ntt830 protein in clarified lysate was pelleted using saturated ammonium sulfate (1:1, vol/vol) overnight at +4° C. Precipitated proteins were solubilized in the buffer A (without mercaptoethanol) for 4 h at +4° C. Insoluble proteins were removed by low speed centrifugation (13,000 rpm, 15 min at 4° C.). Soluble CMV-Ntt830-containing protein solution was separated from cellular proteins by ultracentrifugation (SW28 rotor, Beckman, Palo Alto, USA; at 25,000 rpm, 6 h, 5° C.) in a sucrose gradient (20-60% sucrose in buffer A, without mercaptoethanol, supplemented with 0.5% Triton X-100). The gradient was divided into six fractions, starting at the bottom of the gradient. Fractions containing recombinant CMV-Ntt830 were combined and dialyzed against 200 volumes of 5 mM sodium borate, 2 mM EDTA (pH 9.0) to remove the sucrose and Triton X-100. After dialysis, CMV-Ntt830 solution was sterilized by filtration through a 0.2μ filter. Next, CMV-Ntt830 was concentrated using Type70 rotor (Beckman, Palo Alto, USA) ultracentrifugation through the 20% sucrose "cushion" under sterile conditions (50 000 rpm, 4 h, +5° C.). The concentration of purified CMV-Ntt830 was estimated using the QuBit fluorometer in accordance with manufacturer's recommendations (Invitrogen, Eugene, USA). Concentrated VLP solutions (approx. 3 mg/ml) were stored at +4° C. in 5 mM sodium borate, 2 mM EDTA, buffer (pH 9.0). All steps involved in the expression and purification of VLP were monitored by SDS-PAGE using 12.5% gels. To demonstrate the presence of the tetanus toxoid epitope in CMV VLPs, mass spectrometric analysis of the purified CMV-Ntt830 VLPs was used. As shown in FIG. 3C, the major peak obtained corresponds to the theoretical molecular mass of the protein if the first methionine is removed which occurs during protein synthesis in *E. coli* cells. Dynamic light scattering and electron microscopy confirmed isometric particle morphology similar to CMVwt VLPs (FIGS. 4A and 4B).

Example 5

Cloning of a Modified Coat Protein of CMV Containing a PADRE Epitope

CMV-Npadr

To introduce the PADRE epitope coding sequence in CMVwt gene, PCR mutagenesis was carried out using as the template for amplification and subcloning the pET-CMVwt plasmid (see also Example 2 and 3). For the amplification following primers were used: pET-220 (SEQ ID NO: 11) and CMV-padrSal-R (GACGTCGACGCGCGGCCGCCTT-GAGGGTCCACGC GGCCACAAATTTCGCCATGGT) (SEQ ID NO:15). The resulting PCR product (cDNA of SEQ ID NO:16 coding for CMV-Npadr of SEQ ID NO:7) was again subcloned in BglII/SalI sites of pET-CMVwt. The correct clone was identified by sequencing and designated as pET-CMV-Npadr.

Example 6

Expression of CMV-Npadr in *E. coli* Leading to Modified VLPs of CMV

Figure 5A:
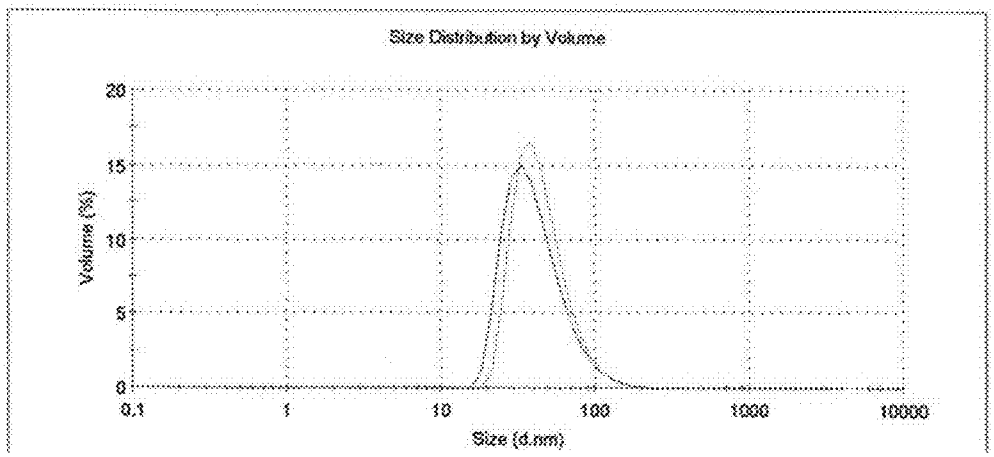
FIG. 5A Dynamic light scattering of purified CMV-Npadr VLPs. The size of particles was detected by using Zetasizer Nano ZS (Malvern Instruments Ltd., United Kingdom).
Figure 5B:
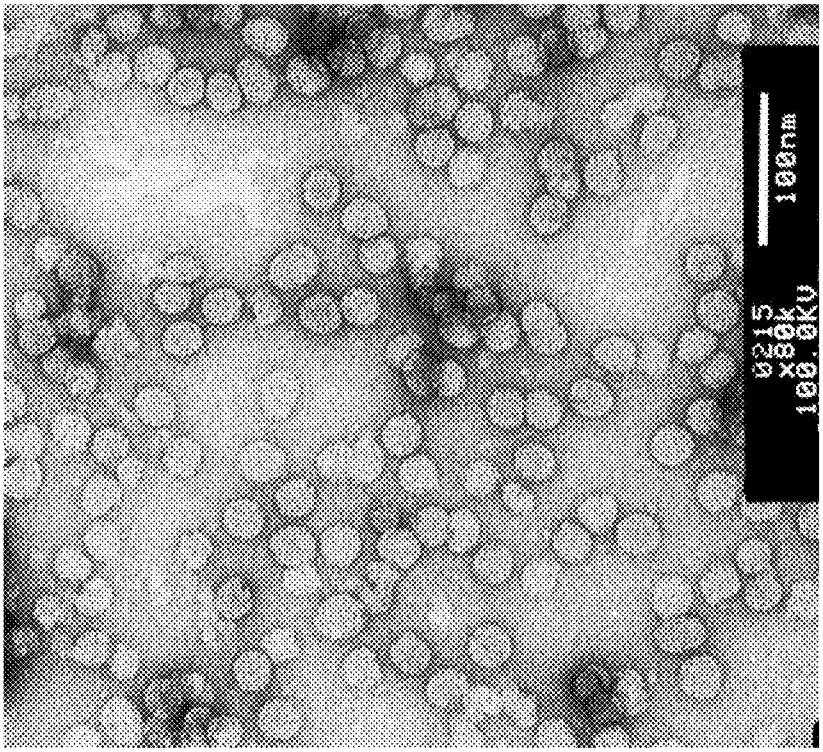
FIG. 5B Electron-microscopy analysis of purified CMV-Npadr VLPs. For the morphological analysis of VLPs the JEM-1230 electron microscope (Jeol Ltd., Tokyo, Japan) was used.

The procedures for expression and purification of CMV-Npadr were essentially the same as for CMV-Ntt830 and are described in Example 4. To demonstrate the presence of the PADRE epitope in CMV VLPs, the mass spectrometric analysis of the purified CMV-Npadr VLPs was used. As shown in FIG. 3B, the major peak obtained corresponds to the theoretical molecular mass of the protein if the first methionine is removed which occurs during protein synthesis in *E. coli* cells. Dynamic light scattering and electron microscopy analysis confirmed isometric particle morphology, (FIG. 5A and FIG. 5B).

Example 7

Cloning and Production of Canine IL-31 with 6×His Tag and C-terminal Cysteine Canine IL31 cDNA sequence with *E. coli* optimised codons, N-terminal 6×His tag, TEV protease cleavage site, C-terminal cysteine and flanking NcoI and PstI restriction sites (SEQ ID NO:17) was manufactured in company IDT. Further, NcoI/PstI fragment was ligated into the corresponding sites of vector pET42. Construct was transformed in chemically competent *E. coli* DH5α cells and colonies were seeded on LB agar plate containing ampicillin. The sequence of resulting clones was verified by Sanger sequencing. The resulting construct pET42_6HcIL31C was further transformed in chemically competent *E. coli* BL21-DE3 cells.

Figure 6:
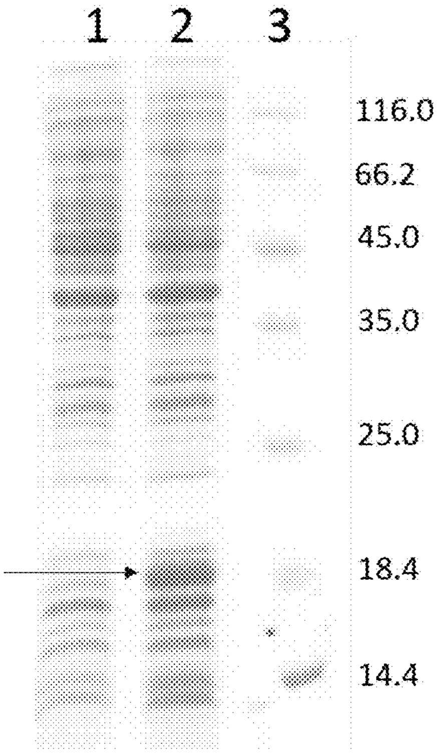
FIG. 6 Production of cIL-31 with 6×His tag and C-terminal cysteine in *E. coli*. Lane 1—total cell lysate before induction, lane 2—total cell lysate after induction, lane 3—marker. Position of cIL-31 protein is indicated with arrow.

Seeding material stock was prepared by seeding IL31-pET42 transformed BL31-DE3 cells into LB medium containing 50 μg/ml ampicillin, and incubating overnight at +37° C. The stock was then added to 2TY medium in volume proportion 1:20. Cells were grown at +37° C. with shaking until optical density at 540 nm reached 0.7 units. Then protein (SEQ ID NO:18) expression was induced with 1 mM IPTG, and cells were grown for additional 4 hours at +37° C. with shaking. Protein production was confirmed by loading the total cell lysate on SDS-PAGE (FIG. 6).

Figure 7:
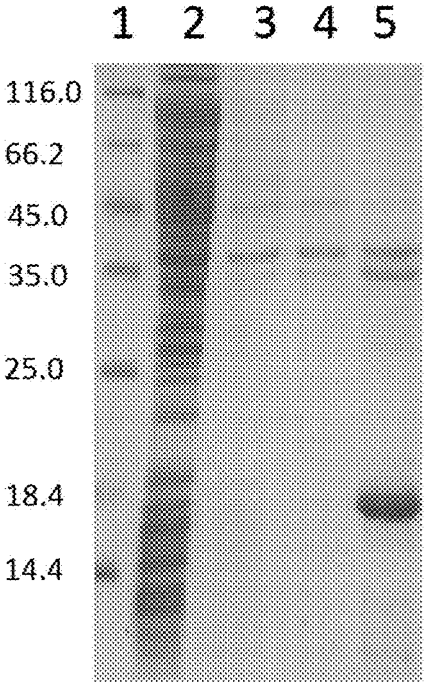
FIG. 7 Purification of cIL-31 with 6×His tag and C-terminal cysteine. Lane 1—marker, lane 2—cell lysate (soluble fraction), lane 2—pellet extraction with wash buffer WB1, lane 2—pellet extraction with wash buffer WB2, lane 3—pellet extraction with elution buffer EB, containing 8M urea.
Figure 8A:
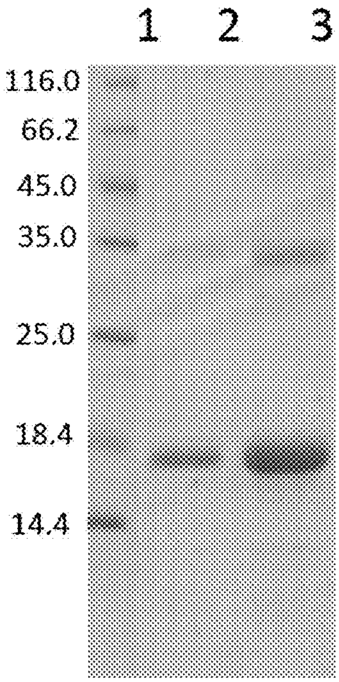
FIG. 8A Refolding of cIL-31 with 6×His tag and C-terminal cysteine. Lane 1—marker, lane 2—insoluble fraction after refolding, lane 3—soluble fraction after refolding.
Figure 8B:
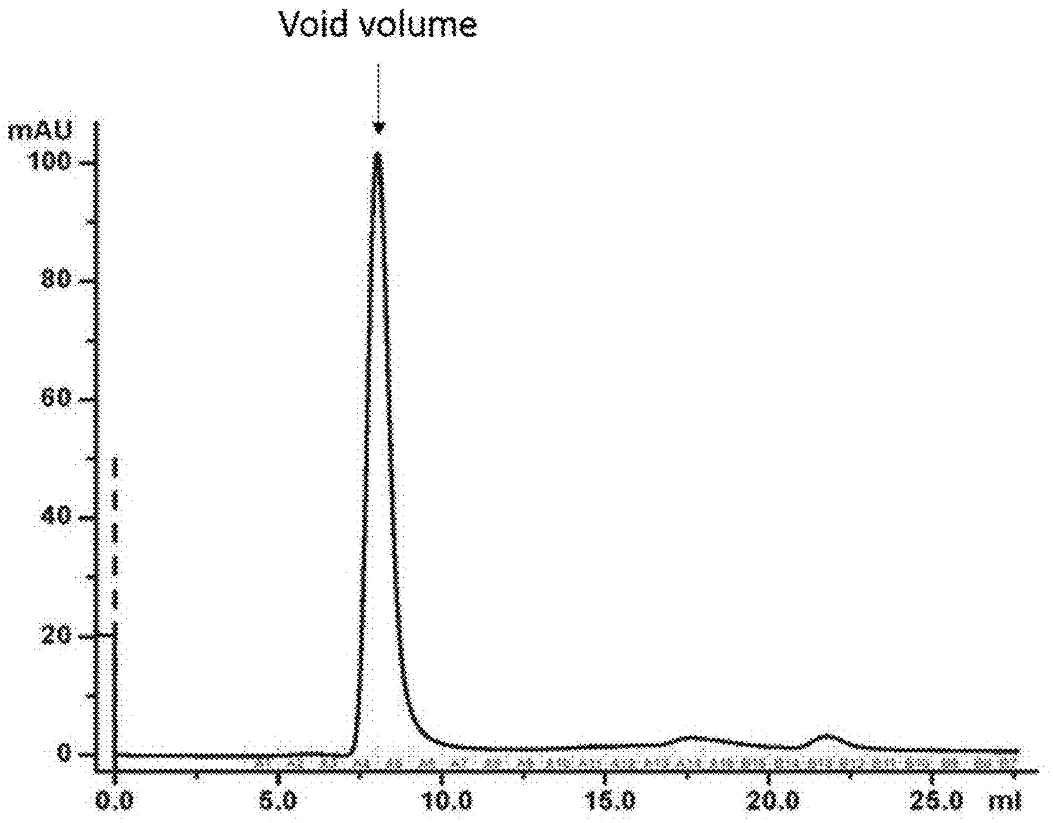
FIG. 8B Gel filtration profile of refolded cIL-31 with 6×His tag and C-terminal cysteine. The peak corresponds to the void volume of column, indicating that material is aggregated.

Biomass was collected with centrifugation and suspended in ice-cold lysis buffer containing 40 mM Tris-HCl (pH 8.0), 200 mM NaCl, 20 mM $MgSO_4$, 0.1 mg/ml DNaseI, 1 mM PMSF and 1% Triton X-100, maintaining proportion of 1 g wet cells per 5 ml of lysis buffer. Cells were lysed with ultrasound sonification on ice, the obtained lysate was centrifuged for 40 min at 15000 g and supernatant discarded. Wash buffer WB1 containing 20 mM Tris HCl, pH=8.0 and 1M NaCl was added to the pellet maintaining proportion of 3 ml WB1 per 1 g of initial wet cell mass. Pellet was resuspended by vortexing and incubated on rotary shaker for 1 h at room temperature and centrifugated for 15 min at 15000 g. Pellet washing was repeated one more time with wash buffer WB2 containing 20 mM Tris HCl, pH=8.0, 200 mM NaCl and 1M urea. Target protein was located in the pellet fraction. Pellet was then resuspended in elution buffer EB1 containing 8 M urea, 20 mM tris HCl, pH=8, and 100 mM $NaH_2PO_4$, maintaining proportion of 3 ml EB1 per 1 g of initial wet cell mass and incubated on rotary shaker at room temperature overnight. After centrifugation, supernatant contained protein with roughly 90% purity (FIG. 7). 1 ml of the obtained supernatant was dropwise added to 20 mL of refolding buffer RB containing 20 mM Tris-HCl, pH=8.0, 50 mM NaCl, 1M glycine, and 5 mM β-mercaptoethanol, and incubated for 2 h at room temperature with stirring. Supernatant was then concentrated to 1 ml by Amicon filter unit (MWCO 10 kDa) and dialysed for 48 h at +4° C. against 1000 ml of PBS. After then, the sample was centrifugated and loaded onto Superdex™ 200 10/300 GL column in PBS. Column profile indicated that target protein is eluted in the void volume and therefore probably forming soluble aggregates (FIG. 8).

Example 8

Cloning and Production of Recombinant Native Canine IL-31

Canine IL-31 was amplified from plasmid, containing SEQ ID NO:17 with PCR, using primers cIL31NATf (TACACCATGGCCTCCCACATGGCTCCAACG, SEQ ID NO:19) and cIL31NATr (CATACTGCAGT-TACTGCGGTCCACTGTTTAAG, SEQ ID NO:20) containing PstI and NcoI sites. The obtained cIL-31 PCR fragment was digested with PstI and NcoI restriction enzymes and ligated in the corresponding sites of pET42 vector. Construct was transformed in chemically competent *E. coli* DH5a cells and colonies were seeded on LB agar plate containing ampicillin. Positive clones were identified by Sanger sequencing. cIL31-pET42 construct was then transformed in chemically competent *E. coli* BL21-DE3 cells.

Figure 9:
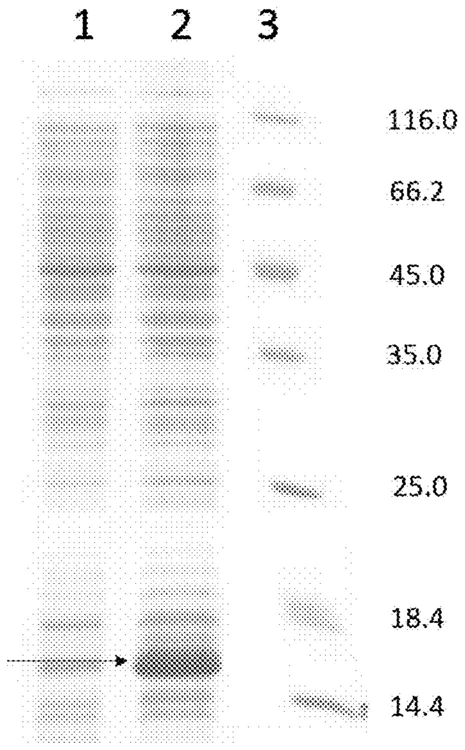
FIG. 9 Production of native recombinant canine cIL-31. Lane 1—total cell lysate before induction, lane 2—total cell lysate after induction, lane 3—marker. Position of cIL-31 protein is indicated with arrow.

Seeding material stock was prepared by seeding cIL31-pET42 transformed BL31-DE3 cells into LB medium containing 50 μg/ml ampicillin, and incubating overnight at +37° C. The stock was then added to 2TY medium in volume proportion 1:20. Cells were grown at +37° C. with shaking until optical density at 540 nm reached 0.7 units. Then protein (SEQ ID NO:21) expression was induced with 1 mM IPTG, and cells were grown for additional 4 hours at +37° C. with shaking. Protein production was confirmed by loading the total cell lysate on SDS-PAGE (FIG. 9).

Figure 10A:
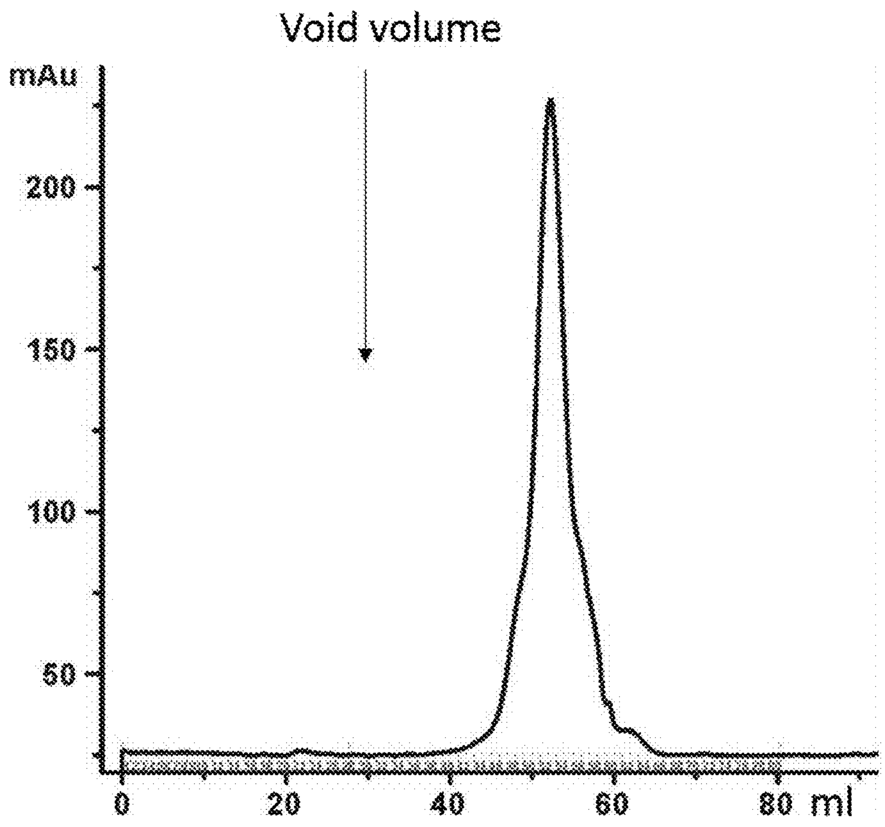
FIG. 10A Purification of refolded native recombinant cIL-31 on gel-filtration column. Protein is eluted much later than column void volume, indicating that material has not aggregated.
Figure 10B:
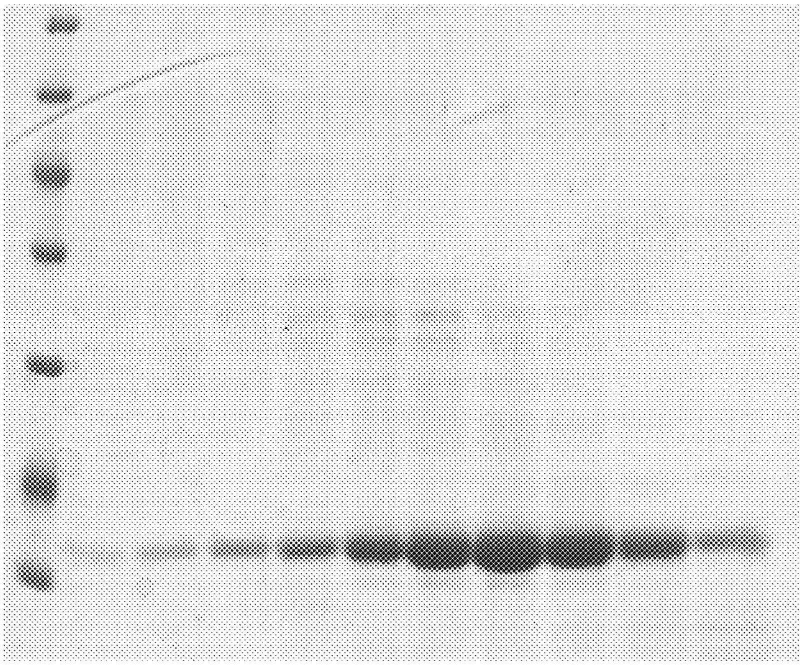
FIG. 10B Analysis of peak fractions on SDS-PAGE

Biomass was collected by centrifugation and suspended in ice-cold lysis buffer containing 40 mM Tris-HCl (pH 8.0), 200 mM NaCl, 20 mM $MgSO_4$, 0.1 mg/ml DNaseI, 1 mM PMSF and 1% Triton X-100, maintaining proportion of 1 g cells per 5 ml of lysis buffer. Cells were lysed with ultrasound sonification on ice and the obtained lysate was centrifuged for 40 min at 15000 g. Supernatant was discarded, and lysis buffer was added to the pellet, maintaining proportion of 1.5 ml of lysis buffer to 1 g of initial wet cell mass. Pellet was suspended in solution by ultrasound sonification, and the solution was centrifuged for 20 min at 15000 g. Supernatant was discarded, and pellet was washed 5 more times with lysis buffer as described above. After washing steps, pellet was re-suspended in 6.86 M urea and 20 mM dithiothreitol by ultrasound sonification. Solution was centrifuged for 20 min at 15000 g, and supernatant was diluted in refolding buffer containing 50 mM Tris-HCl, 1 M glycine, 1 mM EDTA and 5 mM β-mercaptoethanol, maintaining proportion of 75 ml refolding buffer per 1 ml of urea-dithiothreitol solution. Refolding was performed overnight at +4° C. with stirring. The solution was then filtrated using 22 μm filter and concentrated with ultrafiltration using 10 kDa device (Amicon) from 200 ml to 4 ml. The solution was then centrifuged at 15000 g for 10 minutes to remove remaining precipitate. The solution was loaded on Superdex 200 gel filtration column (16×600 mm), previously equilibrated in refolding buffer, and fractionated (2 ml per fraction, flow speed 2 ml/min). Fractions containing cIL-31 protein were identified with SDS-PAGE electrophoresis, pooled and concentrated with ultrafiltration using 10 kDa device (Amicon) to the volume of 3 ml. Re-chromotography was performed on the same Superdex 200 gel filtration column as previously. Column in re-chromatography step was equilibrated in PBS buffer (0.1 M sodium phosphate, pH 7.2 and 0.15 M NaCl). Fractions were analysed with SDS-PAGE electrophoresis (FIG. 10), and four fractions containing the purest cIL-31 protein (SEQ ID NO:21) were pooled, concentrated to 4 mg/ml by ultrafiltration on 10 kDa device (Amicon) and further used for coupling experiments to CMV VLPs.

Example 9

Coupling of Recombinant Canine IL-31 Constructs to CMV-Npadr VLP and CMV-Ntt830 VLP and Immunization of Mice and Dogs A. Coupling of cIL-31 to VLPs 100 μl of solution (4 mg/ml in PBS buffer) of cIL-31 protein (SEQ ID NO:21) as obtained in Example 8 was mixed with 4.8 μl of 55 mM N-succinirnidyl S-acetylthioacetate (SATA, Thermo Fisher Scientific) in DMSO and incubated for 30 min at room temperature (RT). Unreacted SATA was removed by 4× buffer exchange to PBS (0.1 M sodium phosphate buffer, pH 7.2 and 0.15 M NaCl) with Amicon Ultra-0.5 3K filtration units (Merck-Millipore) and final volume adjusted to 100 μl. Sulfhydrylgroups were deprotected by addition of 10 μL of deacetylation solution (0.5 M hydroxylamine and 25 mM EDTA in PBS) and incubation for 2 h at RT. Deacetylation solution was removed by 4× buffer exchange to PBS with Amicon Ultra-0.5 3K filtration units (Merck-Millipore) and final volume adjusted to 100 μl.

CMV-Ntt830 VLP in a volume of 250 μl with a concentration of 1.5 mg/ml in 5 mM NaHPO4 pH 7.5, 2 mM EDTA were mixed with 3 μl of 50 mM succinimidyl-6-(b-maleimidopropionamide) hexanoate (SMPH) solution in DMSO and incubated for 1 hour at RT. The amount of SMPH refers to 7.5× molar excess regarding one VLP monomer, i.e. one CMV polypeptide. Unreacted SMPH was removed by 4× buffer exchange to 5 mM $NaHPO_4$ pH 7.5, 2 mM EDTA pH 8.0 with Amicon Ultra-0.5 3K filtration units (Merck-Millipore) and final volume adjusted to 250 μl.

Figure 11:
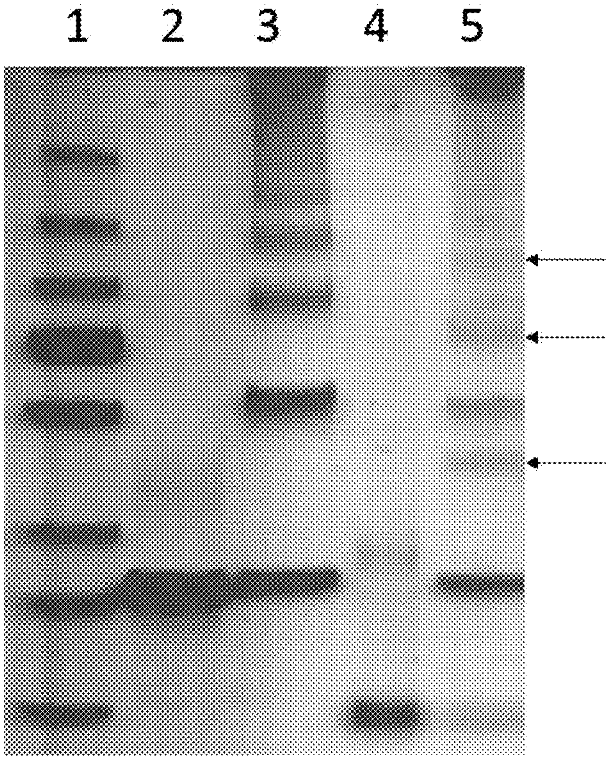
FIG. 11 SDS-PAGE electrophoresis analysis of cIL-31 coupled to CMV VLPs. Lane 1—marker, lane 2—CMV VLPs, lane 3—CMV VLPs, treated with SMPH, lane 4—cIL31, lane 5—cIL-31 coupled to CMV VLPs. The coupling product on lane 5 is indicated with arrows.
Figure 12:
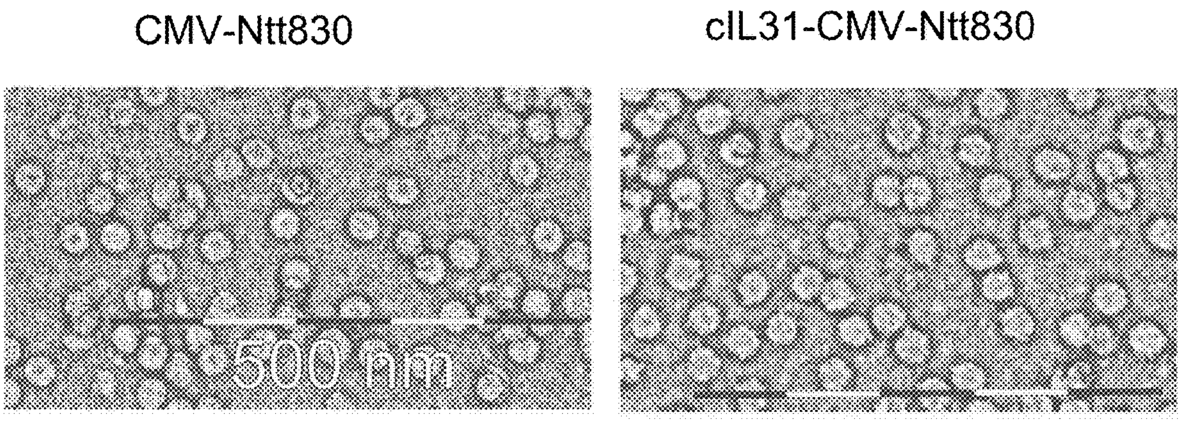
FIG. 12 Electron microscopy of CMV-Ntt830 VLPs and the same VLPs with coupled cIL-31.

For coupling reaction, 100 μl of SMPH-treated VLPs were mixed with 43 μl of SATA-treated and deacetylated cIL-31 of SEQ ID NO:21 and incubated for 3 h at RT. The resulting product was examined by SDS-PAGE (FIG. 11) and electron microscopy (FIG. 12). Analysis on SDS gel confirmed presence of chemical coupling product of expected molecular weight and analysis by EM confirmed presence of intact VLPs.

B. Immunization of Mice with cIL-31 Coupled to CMV-Npadr and CMV-Ntt830 VLPs

Groups of five female Balb/c mice are either immunized s.c. on day 0 and day 14 with 50 ug of CMV-Npadr VLP and CMV-Ntt830 VLP coupled via SATA to cIL-31 of SEQ ID NO:21 formulated in PBS. Mice are bled on days 0 (preimmune), day 14, and day 28, and sera are analyzed using cIL-31 specific ELISA.

ELISA. The antibody response in mouse sera is analyzed at the indicated time. Antibodies specific for cIL-31 is analyzed by coating ELISA plates with a concentration of 5 μg/ml of recombinant cIL-31 in a volume of 100 μl in PBS (pH 7.2) at 4° C. overnight. ELISA plates are washed 5× with 200 μl PBS containing 0.05% Tween20 (pH 7.2, PBST). In order to avoid unspecific binding the ELISA plates are blocked with 200 μl of 2% BSA in PBST and incubated for 2 hours at RT. The serum samples are diluted in 2% BSA/PBST. Pre-diluted sera are transferred onto the coated plates and further serial diluted to obtain antibody titers based on OD50 calculation. After 2 hours of incubation at RT, the ELISA plates are washed 5× with 200 μl of PBST. Binding of serum antibodies is detected by horse-radish peroxidase-conjugated goat anti-mouse IgG (Jackson ImmunoResearch). The detection antibody is diluted 1:1000 in 2% BSA/PBST and a volume of 100 μl per sample was transferred. The plates are incubated for 1 hour at RT. ELISA plates are washed as described before. Prior washing the substrate solution is prepared. To this end, 1 tablet (10 mg) of OPD (1,2-Phenylenediamine dihydrochloride) and 9 μl of 30% $H_2O_2$ is dissolved in 25 ml citric acid buffer (0.066 M $Na_2HPO_4$, 0.035 M citric acid, pH 5.0). A volume of 100 μl of the substrate solution is pipetted onto the plates and exactly incubated for 7 minutes at RT. To stop the reaction 50 μl of stop solution (5% H2SO4 in $H_2O$) is directly pipetted onto the plates. Absorbance readings at 450 nm of the 1,2-Phenylenediamine dihydrochloride color reaction are analyzed.

C. Immunization of Dogs with cIL-31 coupled to CMV-Npadr and CMV-Ntt830 VLPs

Groups of five dogs are either immunized s.c. on day 0 and day 14, day 28 and day 42 with 50 ug of CMV-Npadr VLP and CMV-Ntt830 VLP coupled via SATA to cIL-31 of SEQ ID NO:21 formulated in PBS. Dogs are bled on days 0 (pre-immune), day 14, day 28, day 42 and day 56 and sera are analyzed using cIL-31 specific ELISA.

ELISA. The antibody response in dog sera is analyzed at the indicated time. Antibodies specific for cIL-31 is analyzed by coating ELISA plates with a concentration of 5 μg/ml of recombinant cIL-31 in a volume of 100 μl in PBS (pH 7.2) at 4° C. overnight. ELISA plates are washed 5× with 200 μl PBS containing 0.05% Tween20 (pH 7.2, PBST). In order to avoid unspecific binding the ELISA plates are blocked with 200 μl of 2% BSA in PBST and incubated for 2 hours at RT. The serum samples are diluted in 2% BSA/PBST. Pre-diluted sera are transferred onto the coated plates and further serial diluted to obtain antibody titers based on OD50 calculation. After 2 hours of incubation at RT, the ELISA plates are washed 5× with 200 μl of PBST. Binding of serum antibodies is detected by horse-radish peroxidase-conjugated goat anti-dog IgG (Jackson ImmunoResearch). The detection antibody is diluted 1:1000 in 2% BSA/PBST and a volume of 100 μl per sample was transferred. The plates are incubated for 1 hour at RT. ELISA plates are washed as described before. Prior washing the substrate solution is prepared. To this end, 1 tablet (10 mg) of OPD (1,2-Phenylenediamine dihydrochloride) and 9 μl of 30% $H_2O_2$ is dissolved in 25 ml citric acid buffer (0.066 M $Na_2HPO_4$, 0.035 M citric acid, pH 5.0). A volume of 100 μl of the substrate solution is pipetted onto the plates and exactly incubated for 7 minutes at RT. To stop the reaction 50 μl of stop solution (5% $H_2SO4$ in $H_2O$) is directly pipetted onto the plates. Absorbance readings at 450 nm of the 1,2-Phenylenediamine dihydrochloride color reaction are analyzed.

Example 10

Therapeutic Immunization of Dogs with Recombinant Canine IL-31 Constructs Coupled to CMV-Ntt830 VLP for the Treatment of Canine Atopic Dermatitis Groups of 15 dogs with atopic dermatitis are immunized s.c. on day 0 and day 14, day 28, day 56 and and day 80 with 50 ug CMV-Ntt830 VLP coupled via SATA to cIL-31 of SEQ ID NO:21 or CMV-Ntt830 alone formulated in Alum. Disease severity is measured by visual inspection before immunization and on day 28, day 56, day 80 and day 120.

Example 11

CAD Scoring

For CAD symptom scoring the Atopic Dermatitis Lesion Index (ADLI) and Pruritus Visual Analog Score (PVAS) is used in experimental dogs. The ADLI score is a validated composite index of six clinical symptoms associated with canine atopic dermatitis evaluated in five specified body regions. At each specified body region, each parameter is scored by the scorer from zero to five, with a score of zero defined as no lesion and a score of five defined as a severe/extensive lesions. PVAS is scored by the scorer using a zero to ten analog scale, with a score of zero representing no pruritus/chewing and a score of ten equating to incessant and intense pruritus/chewing. CAD scoring of treated dogs is compared to baseline as well as to scores of dogs treated with placebo.

Example 12

Vaccination of Dogs Allergic to House Dust Mice with cIL-31-CMV-Ntt830 VLP and Challenge Thereafter Six allergic dogs were immunized with 100 ug of cIL-31-CMV-Ntt830 VLPs formulated in Alum and six allergic dogs were treated with placebo (alum). Three weeks later, dogs were boosted with 300 ug vaccine or placebo. Blood was sampled on day 28. On day d-28, hair was removed from abdominal skin by tape stripping, and house dust mite challenge was conducted once daily for ten minutes, for five consecutive days. Skin lesions and pruritus was scored on the 12 dogs through clinical examination videotaping of the dogs for six hours/day.

Figure 13A:
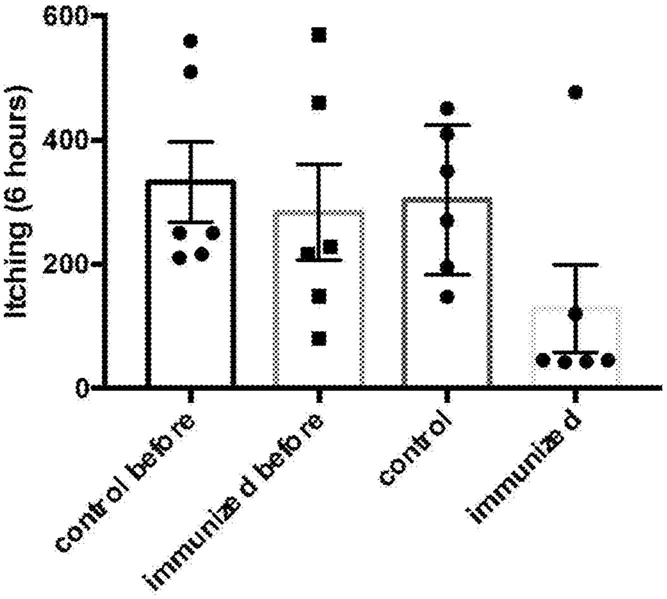
FIG. 13A Vaccination against cIL-31 strongly reduces scratching in immunized allergic dogs. Scratching over 6 hours after challenge with house dust mite extract before and after vaccination.

FIG. 13A shows the scratching behavior of the dogs before and after vaccination. There was a strong reduction in scratching, with 5/6 immunized dogs essentially stopped scratching while the behavior of placebo treated animals did not change.

Figure 13B:
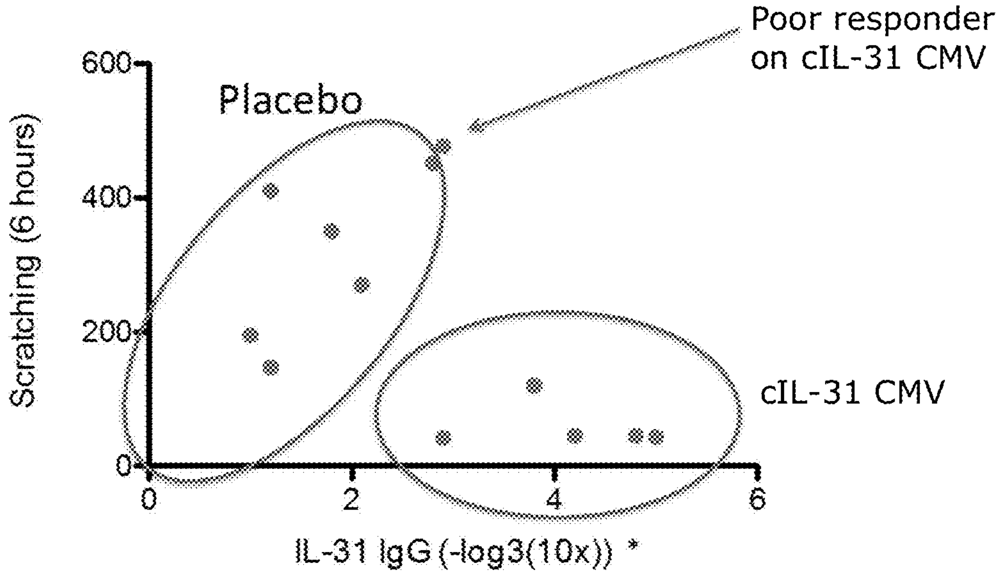
FIG. 13B Correlation of lack of scratching with induction of cIL-31 specific antibodies.

Determination of cIL-31 specific IgG titers. The antibody response in dog sera was analyzed on day 28. Antibodies specific for cIL-31 was analyzed by coating ELISA plates with a concentration of 3 μg/ml of recombinant cIL-31 in a volume of 100 μl in PBS (pH 7.2) at 4° C. overnight. ELISA plates were washed 5× with 200 μl PBS containing 0.05% Tween20 (pH 7.2, PBST). In order to avoid unspecific binding, the ELISA plates were blocked with 200 μl of 2% BSA in PBST and incubated for 2 hours at RT. The serum samples are diluted in 2% BSA/PBST. Pre-diluted sera (10-fold) were transferred onto the coated plates and further serial diluted (3-fold steps) to obtain antibody titers based on OD50 calculation. After 2 hours of incubation at RT, the ELISA plates are washed 5× with 200 μl of PBST. Binding of serum antibodies was detected by horse-radish peroxidase-conjugated goat anti-dog IgG (Jackson ImmunoResearch). The detection antibody was diluted 1:1000 in 2% BSA/PBST and a volume of 100 μl per sample was transferred. The plates were incubated for 1 hour at RT. ELISA plates are washed as described before. Prior washing the 5 substrate solution was prepared. To this end, 1 tablet (10 mg) of OPD (1,2-Phenylenediamine dihydrochloride) and 9 μl of 30% $H_2O2$ was dissolved in 25 ml citric acid buffer (0.066 M Na2HPO4, 0.035 M citric acid, pH 5.0). A volume of 100 μl of the substrate solution was pipetted onto the plates and exactly incubated for 7 minutes at RT. To stop the reaction 50 μl of stop solution (5% H2SO4 in H2O) is directly pipetted onto the plates. Absorbance readings at 450 nm of the 1,2-Phenylenediamine dihydrochloride color reaction were analyzed and expressed as log 3 of 10 fold pre-diluted sera (FIG. 13B). FIG. 13B shows a correlation between IL-31 specific antibody titers and scratching intensity. The one dog that still scratched had mounted the lowest antibody response and an indicative titer of <1/300 was found to be protective.

The invention claimed is:

1. A method of preventing or treating canine atopic dermatitis (CAD) of a canidae, wherein an effective amount of a composition is administered to said canidae, and wherein said composition comprises
   (a) a core particle with at least one first attachment site; and
   (b) at least one canine Interleukin-31 antigen (cIL-31 antigen) with at least one second attachment site, wherein said cIL-31 antigen comprises, a protein with the amino sequence selected from SEQ ID NO:22 or a protein with an amino acid sequence of at least 90%, sequence identity with SEQ ID NO:22;

wherein (a) and (b) are linked through said at least one first and said at least one second attachment site via at least one non-peptide covalent bond.

2. The method of claim 1, wherein said core particle is a virus-like particle (VLP).

3. The method of claim 2, wherein said VLP is derived from a plant virus.

4. The method of claim 2, wherein said VLP is a modified VLP comprising, at least one modified VLP polypeptide, wherein said modified VLP polypeptide comprises,
   (a) a VLP polypeptide, and
   (b) a T helper cell epitope,
   wherein said VLP polypeptide comprises,
   (i) an amino acid sequence of a coat protein of a virus, or
   (ii) a mutated amino acid sequence, wherein the amino acid sequence to be mutated is an amino acid sequence of said coat protein of a virus, and wherein said mutated amino acid sequence and said coat protein of a virus show a sequence identity of at least 90%.

5. The method of claim 2 wherein said VLP is a modified VLP of cucumber mosaic virus (CMV), wherein said modified VLP of CMV comprises, at least one modified CMV polypeptide, wherein said modified CMV polypeptide comprises,
   (a) a CMV polypeptide, and
   (b) a T helper cell epitope; and
   wherein said CMV polypeptide comprises,
   (i) an amino acid sequence of a coat protein of CMV; or
   (ii) a mutated amino acid sequence, wherein the amino acid sequence to be mutated is an amino acid sequence of a coat protein of CMV, and wherein said mutated amino acid sequence and said coat protein of CMV show a sequence identity of at least 90%.

6. The method of claim 5, wherein said CMV polypeptide comprises,
   (a) an amino acid sequence of a coat protein of CMV, wherein said amino acid sequence comprises, SEQ ID NO:1 or
   (b) an amino acid sequence having a sequence identity of at least 90% of SEQ ID NO:1; and wherein said amino sequence as defined in (a) or (b) in this claim comprises SEQ ID NO:23; or wherein said amino sequence as defined in (a) or (b) in this claim comprises an amino acid sequence region, wherein said amino acid sequence region has a sequence identity of at least 90% with SEQ ID NO:23.

7. The method of claim 5, wherein said T helper cell epitope replaces a N-terminal region of said CMV polypeptide, and wherein said N-terminal region of said CMV polypeptide corresponds to amino acids 2-12 of SEQ ID NO:1.

8. The method of claim 5, wherein said Th cell epitope is a PADRE sequence, or wherein said Th cell epitope is derived from tetanus toxin.

9. The method of claim 5, wherein said CMV polypeptide comprises an amino acid sequence of a coat protein of CMV, wherein said amino acid sequence comprises, SEQ ID NO:1 or an amino acid sequence having a sequence identity of at least 95% of SEQ ID NO:1; and wherein said amino sequence comprises SEQ ID NO:23, and wherein said T helper cell epitope replaces the N-terminal region of said CMV polypeptide, and wherein said replaced N-terminal region of said CMV polypeptide consists of 11 to 13 consecutive amino acids.

10. The method of claim 5, wherein said modified CMV polypeptide comprises, an amino acid sequence of SEQ ID NO:6 or SEQ ID NO:7.

11. The method of claim 1, wherein said at least one cIL-31 antigen comprises, a protein with the amino sequence selected from:
   (a) SEQ ID NO:18;
   (b) SEQ ID NO:21;
   (c) SEQ ID NO:22; or
   (d) SEQ ID NO:26.

12. The method of claim 1, wherein said administration of said composition reduces at least one CAD parameter or symptom as compared to said at least one CAD parameter or symptom before said administration, and wherein said at least one CAD parameter or symptom is the level or severity grade of skin lesions or itching.

13. A composition comprising
   (a) a virus-like particle (VLP) with at least one first attachment site;
   (b) at least one canine Interleukin-31 antigen (cIL-31 antigen) with at least one second attachment site, wherein said cIL-31 antigen comprises, a protein with the amino acid sequence selected from SEQ ID NO:22 or a protein with an amino acid sequence of at least 90%, sequence identity with SEQ ID NO:22;

wherein (a) and (b) are linked through said at least one first and said at least one second attachment site via at least one non-peptide covalent bond.

14. A method of claim 8, wherein said Th cell epitope comprises the amino acid sequence of SEQ ID NO:5, or wherein said Th cell epitope has the amino acid sequence of SEQ ID NO:4.

15. The composition of claim 13, wherein said VLP is a modified VLP of cucumber mosaic virus (CMV) comprising at least one modified CMV polypeptide, wherein said modified CMV polypeptide comprises (a) a CMV polypeptide, and (b) a T helper cell epitope; and wherein said CMV polypeptide comprises (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said coat protein of CMV show a sequence identity of at least 90%.

16. The composition of claim 15, wherein said Th cell epitope is a PADRE sequence, or wherein said Th cell epitope is derived from tetanus toxin.

17. The composition of claim 15, wherein said Th cell epitope comprises the amino acid sequence of SEQ ID NO:5, or wherein said Th cell epitope comprises the amino acid sequence of SEQ ID NO:4.

18. The composition of claim 13 wherein said modified CMV polypeptide comprises, the amino acid sequence of SEQ ID NO:6 or SEQ ID NO:7.

19. The composition of claim 13, wherein said at least one cIL-31 antigen comprises a protein with the amino sequence selected from:

(a) SEQ ID NO:18;

(b) SEQ ID NO:21;

(c) SEQ ID NO:22; or (d) SEQ ID NO:26.

* * * * *

SEQUENCE LISTING

```
<160> NUMBER OF SEQ ID NOS: 30

<210> SEQ ID NO 1
<211> LENGTH: 218
<212> TYPE: PRT
<213> ORGANISM: cucumber mosaic virus

<400> SEQUENCE: 1

Met Asp Lys Ser Glu Ser Thr Ser Ala Gly Arg Ser Arg Arg Arg Arg
1               5                   10                  15

Pro Arg Arg Gly Ser Arg Ser Ala Pro Ser Ser Ala Asp Ala Asn Phe
            20                  25                  30

Arg Val Leu Ser Gln Gln Leu Ser Arg Leu Asn Lys Thr Leu Ala Ala
        35                  40                  45

Gly Arg Pro Thr Ile Asn His Pro Thr Phe Val Gly Ser Glu Arg Cys
    50                  55                  60

Lys Pro Gly Tyr Thr Phe Thr Ser Ile Thr Leu Lys Pro Pro Lys Ile
65                  70                  75                  80

Asp Arg Gly Ser Tyr Tyr Gly Lys Arg Leu Leu Leu Pro Asp Ser Val
                85                  90                  95

Thr Glu Tyr Asp Lys Lys Leu Val Ser Arg Ile Gln Ile Arg Val Asn
            100                 105                 110

Pro Leu Pro Lys Phe Asp Ser Thr Val Trp Val Thr Val Arg Lys Val
        115                 120                 125

Pro Ala Ser Ser Asp Leu Ser Val Ala Ala Ile Ser Ala Met Phe Ala
    130                 135                 140

Asp Gly Ala Ser Pro Val Leu Val Tyr Gln Tyr Ala Ala Ser Gly Val
145                 150                 155                 160

Gln Ala Asn Asn Lys Leu Leu Tyr Asp Leu Ser Ala Met Arg Ala Asp
                165                 170                 175

Ile Gly Asp Met Arg Lys Tyr Ala Val Leu Val Tyr Ser Lys Asp Asp
            180                 185                 190

Ala Leu Glu Thr Asp Glu Leu Val Leu His Val Asp Val Glu His Gln
        195                 200                 205

Arg Ile Pro Thr Ser Gly Val Leu Pro Val
    210                 215


<210> SEQ ID NO 2
<211> LENGTH: 217
<212> TYPE: PRT
<213> ORGANISM: cucumber mosaic virus

<400> SEQUENCE: 2

Asp Lys Ser Glu Ser Thr Ser Ala Gly Arg Asn Arg Arg Arg Arg Pro
1               5                   10                  15

Arg Arg Gly Ser Arg Ser Ala Ser Ser Ser Ala Asp Ala Asn Phe Arg
            20                  25                  30

Val Leu Ser Gln Gln Leu Ser Arg Leu Asn Lys Thr Leu Ala Ala Gly
        35                  40                  45

Arg Pro Thr Ile Asn His Pro Thr Phe Val Gly Ser Glu Arg Cys Lys
    50                  55                  60

Pro Gly Tyr Thr Phe Ser Ser Ile Thr Leu Lys Pro Pro Lys Ile Asp
65                  70                  75                  80

Arg Gly Ser Tyr Tyr Gly Lys Arg Leu Leu Leu Pro Asp Ser Val Thr
                85                  90                  95

Glu Phe Asp Lys Lys Leu Val Ser Arg Ile Gln Ile Arg Val Asn Pro
```

-continued

```
            100                 105                 110

Leu Pro Lys Phe Asp Ser Thr Val Trp Val Thr Val Arg Lys Val Pro
        115                 120                 125

Ala Ser Ser Asp Leu Ser Val Ala Ala Ile Ser Ala Met Phe Ala Asp
    130                 135                 140

Gly Ala Ser Pro Val Leu Val Tyr Gln Tyr Ala Ala Ser Gly Val Gln
145                 150                 155                 160

Ala Asn Asn Lys Leu Leu Tyr Asp Leu Ser Ala Met Arg Ala Asp Ile
                165                 170                 175

Gly Asp Met Arg Lys Tyr Ala Val Leu Val Tyr Ser Lys Asp Asp Ala
            180                 185                 190

Leu Glu Thr Asp Glu Leu Val Leu His Val Asp Ile Glu His Gln Arg
        195                 200                 205

Ile Pro Thr Ser Gly Val Leu Pro Val
    210                 215


<210> SEQ ID NO 3
<211> LENGTH: 218
<212> TYPE: PRT
<213> ORGANISM: cucumber mosaic virus

<400> SEQUENCE: 3

Met Asp Lys Ser Glu Ser Pro Asn Ala Ser Arg Thr Ser Arg Arg Arg
1               5                   10                  15

Arg Pro Arg Arg Gly Ser Arg Ser Ala Ser Gly Ala Asp Ala Gly Leu
            20                  25                  30

Arg Ala Leu Thr Gln Gln Met Leu Lys Leu Asn Lys Thr Leu Ala Ile
        35                  40                  45

Gly Arg Pro Thr Leu Asn His Pro Thr Phe Val Gly Ser Ala Ser Cys
    50                  55                  60

Lys Pro Gly Tyr Thr Phe Thr Ser Ile Thr Leu Lys Pro Pro Glu Ile
65                  70                  75                  80

Glu Lys Gly Ser Tyr Phe Gly Arg Arg Leu Ser Leu Pro Asp Ser Val
                85                  90                  95

Thr Asp Tyr Asp Lys Lys Leu Val Ser Arg Ile Gln Ile Arg Ile Asn
            100                 105                 110

Pro Leu Pro Lys Phe Asp Ser Thr Val Trp Val Thr Val Arg Lys Val
        115                 120                 125

Pro Ser Ser Ser Asp Leu Ser Val Ala Thr Ile Ser Ala Met Phe Gly
    130                 135                 140

Asp Gly Asn Ser Pro Val Leu Val Tyr Gln Tyr Thr Ala Ser Gly Val
145                 150                 155                 160

Gln Ala Asn Asn Lys Leu Leu Tyr Asp Leu Ser Glu Met Arg Ala Asp
                165                 170                 175

Ile Gly Asp Met Arg Lys Tyr Ala Val Leu Val Tyr Ser Lys Asp Asp
            180                 185                 190

Lys Leu Glu Glu Asp Glu Ile Val Leu His Val Asp Val Glu His Gln
        195                 200                 205

Arg Ile Pro Ile Ser Arg Met Leu Pro Thr
    210                 215


<210> SEQ ID NO 4
<211> LENGTH: 14
<212> TYPE: PRT
<213> ORGANISM: artificial sequence
<220> FEATURE:
```

<223> OTHER INFORMATION: tetanus toxoid epitope tt830

<400> SEQUENCE: 4

Gln Tyr Ile Lys Ala Asn Ser Lys Phe Ile Gly Ile Thr Glu
1 5 10

<210> SEQ ID NO 5
<211> LENGTH: 13
<212> TYPE: PRT
<213> ORGANISM: artificial sequence
<220> FEATURE:
<223> OTHER INFORMATION: PADRE

<400> SEQUENCE: 5

Ala Lys Phe Val Ala Ala Trp Thr Leu Lys Ala Ala Ala
1 5 10

<210> SEQ ID NO 6
<211> LENGTH: 222
<212> TYPE: PRT
<213> ORGANISM: artificial sequence
<220> FEATURE:
<223> OTHER INFORMATION: CMV-Ntt830

<400> SEQUENCE: 6

Met Gly Gln Tyr Ile Lys Ala Asn Ser Lys Phe Ile Gly Ile Thr Glu
1 5 10 15

Arg Arg Arg Arg Pro Arg Arg Gly Ser Arg Ser Ala Pro Ser Ser Ala
20 25 30

Asp Ala Asn Phe Arg Val Leu Ser Gln Gln Leu Ser Arg Leu Asn Lys
35 40 45

Thr Leu Ala Ala Gly Arg Pro Thr Ile Asn His Pro Thr Phe Val Gly
50 55 60

Ser Glu Arg Cys Lys Pro Gly Tyr Thr Phe Thr Ser Ile Thr Leu Lys
65 70 75 80

Pro Pro Lys Ile Asp Arg Gly Ser Tyr Tyr Gly Lys Arg Leu Leu Leu
85 90 95

Pro Asp Ser Val Thr Glu Tyr Asp Lys Lys Leu Val Ser Arg Ile Gln
100 105 110

Ile Arg Val Asn Pro Leu Pro Lys Phe Asp Ser Thr Val Trp Val Thr
115 120 125

Val Arg Lys Val Pro Ala Ser Ser Asp Leu Ser Val Ala Ala Ile Ser
130 135 140

Ala Met Phe Ala Asp Gly Ala Ser Pro Val Leu Val Tyr Gln Tyr Ala
145 150 155 160

Ala Ser Gly Val Gln Ala Asn Asn Lys Leu Leu Tyr Asp Leu Ser Ala
165 170 175

Met Arg Ala Asp Ile Gly Asp Met Arg Lys Tyr Ala Val Leu Val Tyr
180 185 190

Ser Lys Asp Asp Ala Leu Glu Thr Asp Glu Leu Val Leu His Val Asp
195 200 205

Val Glu His Gln Arg Ile Pro Thr Ser Gly Val Leu Pro Val
210 215 220

<210> SEQ ID NO 7
<211> LENGTH: 220
<212> TYPE: PRT
<213> ORGANISM: artificial sequence
<220> FEATURE:
<223> OTHER INFORMATION: CMV-Npadr

<400> SEQUENCE: 7

```
Met Ala Lys Phe Val Ala Ala Trp Thr Leu Lys Ala Ala Ala Arg Arg
1               5                   10                  15

Arg Arg Pro Arg Arg Gly Ser Arg Ser Ala Pro Ser Ser Ala Asp Ala
            20                  25                  30

Asn Phe Arg Val Leu Ser Gln Gln Leu Ser Arg Leu Asn Lys Thr Leu
        35                  40                  45

Ala Ala Gly Arg Pro Thr Ile Asn His Pro Thr Phe Val Gly Ser Glu
    50                  55                  60

Arg Cys Lys Pro Gly Tyr Thr Phe Thr Ser Ile Thr Leu Lys Pro Pro
65                  70                  75                  80

Lys Ile Asp Arg Gly Ser Tyr Tyr Gly Lys Arg Leu Leu Leu Pro Asp
                85                  90                  95

Ser Val Thr Glu Tyr Asp Lys Lys Leu Val Ser Arg Ile Gln Ile Arg
            100                 105                 110

Val Asn Pro Leu Pro Lys Phe Asp Ser Thr Val Trp Val Thr Val Arg
        115                 120                 125

Lys Val Pro Ala Ser Ser Asp Leu Ser Val Ala Ala Ile Ser Ala Met
    130                 135                 140

Phe Ala Asp Gly Ala Ser Pro Val Leu Val Tyr Gln Tyr Ala Ala Ser
145                 150                 155                 160

Gly Val Gln Ala Asn Asn Lys Leu Leu Tyr Asp Leu Ser Ala Met Arg
                165                 170                 175

Ala Asp Ile Gly Asp Met Arg Lys Tyr Ala Val Leu Val Tyr Ser Lys
            180                 185                 190

Asp Asp Ala Leu Glu Thr Asp Glu Leu Val Leu His Val Asp Val Glu
        195                 200                 205

His Gln Arg Ile Pro Thr Ser Gly Val Leu Pro Val
    210                 215                 220
```

<210> SEQ ID NO 8
<211> LENGTH: 34
<212> TYPE: DNA
<213> ORGANISM: artificial sequence
<220> FEATURE:
<223> OTHER INFORMATION: primer CMcpF

<400> SEQUENCE: 8
caccatggac aaatctgaat caaccagtgc tggt 34

<210> SEQ ID NO 9
<211> LENGTH: 37
<212> TYPE: DNA
<213> ORGANISM: artificial sequence
<220> FEATURE:
<223> OTHER INFORMATION: primer CMcpR

<400> SEQUENCE: 9
caaagcttat caaactggga gcaccccaga tgtggga 37

<210> SEQ ID NO 10
<211> LENGTH: 660
<212> TYPE: DNA
<213> ORGANISM: cucumber mosaic virus

<400> SEQUENCE: 10
atggacaaat ctgaatcaac cagtgctggt cgtagccgtc gacgtcgtcc gcgtcgtggt 60

-continued tcccgctccg ccccctcctc cgcggatgct aactttagag tcttgtcgca gcagctttcg 120
cgacttaata agacgttagc agctggtcgt ccaactatta accacccaac ctttgtaggg 180
agtgaacgct gtaaacctgg gtacacgttc acatctatca ccctaaagcc accaaaaata 240
gaccgtgggt cttattatgg taaaaggttg ttattacctg attcagtcac ggaatatgat 300
aagaaacttg tttcgcgcat tcaaattcga gttaatcctt tgccgaaatt tgattcaacc 360
gtgtgggtga cagtccgtaa agttcctgcc tcttcggact tatccgttgc cgccatttct 420
gctatgtttg cggacggagc ctcaccggta ctggtttatc agtacgctgc atctggagtc 480
caagctaaca acaaactgtt gtatgatctt tcggcgatgc gcgctgatat aggcgacatg 540
agaaagtacg ccgtcctcgt gtattcaaaa gacgatgcac tcgagacaga cgagttagta 600
cttcatgttg acgtcgagca ccaacgtatt cccacatctg ggtgctcccc agtttgataa 660

<210> SEQ ID NO 11
<211> LENGTH: 20
<212> TYPE: DNA
<213> ORGANISM: artificial sequence
<220> FEATURE:
<223> OTHER INFORMATION: primer pET-220

<400> SEQUENCE: 11
agcaccgccg ccgcaaggaa 20

<210> SEQ ID NO 12
<211> LENGTH: 52
<212> TYPE: DNA
<213> ORGANISM: artificial sequence
<220> FEATURE:
<223> OTHER INFORMATION: primer CMV-tt83-1R

<400> SEQUENCE: 12
atttggagtt ggccttaata tactggccca tggtatatct ccttcttaaa gt 52

<210> SEQ ID NO 13
<211> LENGTH: 52
<212> TYPE: DNA
<213> ORGANISM: artificial sequence
<220> FEATURE:
<223> OTHER INFORMATION: primer CMV-tt83Sal-R2

<400> SEQUENCE: 13
gacgtcgacg ctcggtaatc ccgataaatt tggagttggc cttaatatac tg 52

<210> SEQ ID NO 14
<211> LENGTH: 672
<212> TYPE: DNA
<213> ORGANISM: artificial sequence
<220> FEATURE:
<223> OTHER INFORMATION: cDNA coding for CMV-Ntt830

<400> SEQUENCE: 14
atgggccagt atattaaggc caactccaaa tttatcggga ttaccgagcg tcgacgtcgt 60
ccgcgtcgtg gttcccgctc cgccccctcc tccgcggatg ctaactttag agtcttgtcg 120
cagcagcttt cgcgacttaa taagacgtta gcagctggtc gtccaactat taaccaccca 180
acctttgtag ggagtgaacg ctgtaaacct gggtacacgt tcacatctat caccctaaag 240
ccaccaaaaa tagaccgtgg gtcttattat ggtaaaaggt tgttattacc tgattcagtc 300
acggaatatg ataagaaact tgtttcgcgc attcaaattc gagttaatcc tttgccgaaa 360
tttgattcaa ccgtgtgggt gacagtccgt aaagttcctg cctcttcgga cttatccgtt 420
gccgccattt ctgctatgtt tgcggacgga gcctcaccgg tactggttta tcagtacgct 480
gcatctggag tccaagctaa caacaaactg ttgtatgatc tttcggcgat gcgcgctgat 540
ataggcgaca tgagaaagta cgccgtcctc gtgtattcaa aagacgatgc actcgagaca 600
gacgagttag tacttcatgt tgacgtcgag caccaacgta ttcccacatc tggggtgctc 660
ccagtttgat aa 672

<210> SEQ ID NO 15
<211> LENGTH: 55
<212> TYPE: DNA
<213> ORGANISM: artificial sequence
<220> FEATURE:
<223> OTHER INFORMATION: primer CMV-padrSal-R

<400> SEQUENCE: 15
gacgtcgacg cgcggccgcc ttgagggtcc acgcggccac aaatttcgcc atggt 55

<210> SEQ ID NO 16
<211> LENGTH: 666
<212> TYPE: DNA
<213> ORGANISM: artificial sequence
<220> FEATURE:
<223> OTHER INFORMATION: cDNA coding for CMV-Npadr

<400> SEQUENCE: 16
atggcgaaat ttgtggccgc gtggaccctc aaggcggccg cgcgtcgacg tcgtccgcgt 60
cgtggttccc gctccgcccc ctcctccgcg gatgctaact ttagagtctt gtcgcagcag 120
ctttcgcgac ttaataagac gttagcagct ggtcgtccaa ctattaacca cccaaccttt 180
gtagggagtg aacgctgtaa acctgggtac acgttcacat ctatcaccct aaagccacca 240
aaaatagacc gtgggtctta ttatggtaaa aggttgttat tacctgattc agtcacggaa 300
tatgataaga aacttgtttc gcgcattcaa attcgagtta atcctttgcc gaaatttgat 360
tcaaccgtgt gggtgacagt ccgtaaagtt cctgcctctt cggacttatc cgttgccgcc 420
atttctgcta tgtttgcgga cggagcctca ccggtactgg tttatcagta cgctgcatct 480
ggagtccaag ctaacaacaa actgttgtat gatctttcgg cgatgcgcgc tgatataggc 540
gacatgagaa agtacgccgt cctcgtgtat tcaaaagacg atgcactcga gacagacgag 600
ttagtacttc atgttgacgt cgagcaccaa cgtattccca catctggggt gctcccagtt 660
tgataa 666

<210> SEQ ID NO 17
<211> LENGTH: 464
<212> TYPE: DNA
<213> ORGANISM: artificial sequence
<220> FEATURE:
<223> OTHER INFORMATION: cDNA His6/TEV/C

<400> SEQUENCE: 17
ccatggccca tcatcaccat catcacgaaa acctgtactt tcaatcccac atggctccaa 60
cgcatcagct gcctccatcc gatgtgcgca agatcattct ggaactccag ccgctcagcc 120
gtggactgtt agaagactac cagaagaaag aaacgggggt cccagaatct aaccgtacgc 180
tgctgctgtg cctgacgagc gatagccagc ctcctcgtct gaacagctcc gcgatcttac 240
cctactttcg tgccatccgc cctctgtccg ataagaatat tattgacaaa atcattgagc 300
aactggataa gctgaaattt cagcacgaac ctgagacgga gattagtgtc ccggcggata 360

-continued cgtttgaatg taagagtttt atcctcacaa ttctccagca attttctgcg tgcttggaat 420
cagtatttaa gtccttaaac agtggaccgc agtgctaact gcag 464

<210> SEQ ID NO 18
<211> LENGTH: 151
<212> TYPE: PRT
<213> ORGANISM: artificial sequence
<220> FEATURE:
<223> OTHER INFORMATION: cIL-31-His6/TEV/C

<400> SEQUENCE: 18

Met Ala His His His His His His Glu Asn Leu Tyr Phe Gln Ser His
1 5 10 15

Met Ala Pro Thr His Gln Leu Pro Pro Ser Asp Val Arg Lys Ile Ile
20 25 30

Leu Glu Leu Gln Pro Leu Ser Arg Gly Leu Leu Glu Asp Tyr Gln Lys
35 40 45

Lys Glu Thr Gly Val Pro Glu Ser Asn Arg Thr Leu Leu Leu Cys Leu
50 55 60

Thr Ser Asp Ser Gln Pro Pro Arg Leu Asn Ser Ser Ala Ile Leu Pro
65 70 75 80

Tyr Phe Arg Ala Ile Arg Pro Leu Ser Asp Lys Asn Ile Ile Asp Lys
85 90 95

Ile Ile Glu Gln Leu Asp Lys Leu Lys Phe Gln His Glu Pro Glu Thr
100 105 110

Glu Ile Ser Val Pro Ala Asp Thr Phe Glu Cys Lys Ser Phe Ile Leu
115 120 125

Thr Ile Leu Gln Gln Phe Ser Ala Cys Leu Glu Ser Val Phe Lys Ser
130 135 140

Leu Asn Ser Gly Pro Gln Cys
145 150

<210> SEQ ID NO 19
<211> LENGTH: 30
<212> TYPE: DNA
<213> ORGANISM: artificial sequence
<220> FEATURE:
<223> OTHER INFORMATION: forward primer cIL31NATf

<400> SEQUENCE: 19
tacaccatgg cctcccacat ggctccaacg 30

<210> SEQ ID NO 20
<211> LENGTH: 32
<212> TYPE: DNA
<213> ORGANISM: artificial sequence
<220> FEATURE:
<223> OTHER INFORMATION: reverse primer cIL31NATr

<400> SEQUENCE: 20
catactgcag ttactgcggt ccactgttta ag 32

<210> SEQ ID NO 21
<211> LENGTH: 138
<212> TYPE: PRT
<213> ORGANISM: artificial sequence
<220> FEATURE:
<223> OTHER INFORMATION: cIL-31/A

<400> SEQUENCE: 21

Met Ala Ser His Met Ala Pro Thr His Gln Leu Pro Pro Ser Asp Val

```
1               5                   10                  15

Arg Lys Ile Ile Leu Glu Leu Gln Pro Leu Ser Arg Gly Leu Leu Glu
            20                  25                  30

Asp Tyr Gln Lys Lys Glu Thr Gly Val Pro Glu Ser Asn Arg Thr Leu
        35                  40                  45

Leu Leu Cys Leu Thr Ser Asp Ser Gln Pro Pro Arg Leu Asn Ser Ser
    50                  55                  60

Ala Ile Leu Pro Tyr Phe Arg Ala Ile Arg Pro Leu Ser Asp Lys Asn
65                  70                  75                  80

Ile Ile Asp Lys Ile Ile Glu Gln Leu Asp Lys Leu Lys Phe Gln His
                85                  90                  95

Glu Pro Glu Thr Glu Ile Ser Val Pro Ala Asp Thr Phe Glu Cys Lys
            100                 105                 110

Ser Phe Ile Leu Thr Ile Leu Gln Gln Phe Ser Ala Cys Leu Glu Ser
        115                 120                 125

Val Phe Lys Ser Leu Asn Ser Gly Pro Gln
    130                 135
```

<210> SEQ ID NO 22
<211> LENGTH: 136
<212> TYPE: PRT
<213> ORGANISM: artificial sequence
<220> FEATURE:
<223> OTHER INFORMATION: cIL31

<400> SEQUENCE: 22

```
Ser His Met Ala Pro Thr His Gln Leu Pro Pro Ser Asp Val Arg Lys
1               5                   10                  15

Ile Ile Leu Glu Leu Gln Pro Leu Ser Arg Gly Leu Leu Glu Asp Tyr
            20                  25                  30

Gln Lys Lys Glu Thr Gly Val Pro Glu Ser Asn Arg Thr Leu Leu Leu
        35                  40                  45

Cys Leu Thr Ser Asp Ser Gln Pro Pro Arg Leu Asn Ser Ser Ala Ile
    50                  55                  60

Leu Pro Tyr Phe Arg Ala Ile Arg Pro Leu Ser Asp Lys Asn Ile Ile
65                  70                  75                  80

Asp Lys Ile Ile Glu Gln Leu Asp Lys Leu Lys Phe Gln His Glu Pro
                85                  90                  95

Glu Thr Glu Ile Ser Val Pro Ala Asp Thr Phe Glu Cys Lys Ser Phe
            100                 105                 110

Ile Leu Thr Ile Leu Gln Gln Phe Ser Ala Cys Leu Glu Ser Val Phe
        115                 120                 125

Lys Ser Leu Asn Ser Gly Pro Gln
    130                 135
```

<210> SEQ ID NO 23
<211> LENGTH: 27
<212> TYPE: PRT
<213> ORGANISM: artificial Sequence
<220> FEATURE:
<223> OTHER INFORMATION: fragment of CMV coat protein

<400> SEQUENCE: 23

```
Asp Lys Ser Glu Ser Thr Ser Ala Gly Arg Ser Arg Arg Arg Arg Pro
1               5                   10                  15

Arg Arg Gly Ser Arg Ser Ala Pro Ser Ser Ala
            20                  25
```

-continued

<210> SEQ ID NO 24
<211> LENGTH: 10
<212> TYPE: DNA
<213> ORGANISM: artificial sequence
<220> FEATURE:
<223> OTHER INFORMATION: palindromic CpG

<400> SEQUENCE: 24
gacgatcgtc 10

<210> SEQ ID NO 25
<211> LENGTH: 150
<212> TYPE: PRT
<213> ORGANISM: artificial sequence
<220> FEATURE:
<223> OTHER INFORMATION: cIL-31-A/His6/TEV/C

<400> SEQUENCE: 25

Ala His His His His His His Glu Asn Leu Tyr Phe Gln Ser His Met
1 5 10 15

Ala Pro Thr His Gln Leu Pro Pro Ser Asp Val Arg Lys Ile Ile Leu
20 25 30

Glu Leu Gln Pro Leu Ser Arg Gly Leu Leu Glu Asp Tyr Gln Lys Lys
35 40 45

Glu Thr Gly Val Pro Glu Ser Asn Arg Thr Leu Leu Leu Cys Leu Thr
50 55 60

Ser Asp Ser Gln Pro Pro Arg Leu Asn Ser Ser Ala Ile Leu Pro Tyr
65 70 75 80

Phe Arg Ala Ile Arg Pro Leu Ser Asp Lys Asn Ile Ile Asp Lys Ile
85 90 95

Ile Glu Gln Leu Asp Lys Leu Lys Phe Gln His Glu Pro Glu Thr Glu
100 105 110

Ile Ser Val Pro Ala Asp Thr Phe Glu Cys Lys Ser Phe Ile Leu Thr
115 120 125

Ile Leu Gln Gln Phe Ser Ala Cys Leu Glu Ser Val Phe Lys Ser Leu
130 135 140

Asn Ser Gly Pro Gln Cys
145 150

<210> SEQ ID NO 26
<211> LENGTH: 137
<212> TYPE: PRT
<213> ORGANISM: artificial sequence
<220> FEATURE:
<223> OTHER INFORMATION: cIL-31/AoM

<400> SEQUENCE: 26

Ala Ser His Met Ala Pro Thr His Gln Leu Pro Pro Ser Asp Val Arg
1 5 10 15

Lys Ile Ile Leu Glu Leu Gln Pro Leu Ser Arg Gly Leu Leu Glu Asp
20 25 30

Tyr Gln Lys Lys Glu Thr Gly Val Pro Glu Ser Asn Arg Thr Leu Leu
35 40 45

Leu Cys Leu Thr Ser Asp Ser Gln Pro Pro Arg Leu Asn Ser Ser Ala
50 55 60

Ile Leu Pro Tyr Phe Arg Ala Ile Arg Pro Leu Ser Asp Lys Asn Ile
65 70 75 80

Ile Asp Lys Ile Ile Glu Gln Leu Asp Lys Leu Lys Phe Gln His Glu
85 90 95

```
Pro Glu Thr Glu Ile Ser Val Pro Ala Asp Thr Phe Glu Cys Lys Ser
            100                 105                 110

Phe Ile Leu Thr Ile Leu Gln Gln Phe Ser Ala Cys Leu Glu Ser Val
        115                 120                 125

Phe Lys Ser Leu Asn Ser Gly Pro Gln
    130                 135


<210> SEQ ID NO 27
<211> LENGTH: 150
<212> TYPE: PRT
<213> ORGANISM: artificial sequence
<220> FEATURE:
<223> OTHER INFORMATION: cIL-31-His6/TEV

<400> SEQUENCE: 27

Met Ala His His His His His His Glu Asn Leu Tyr Phe Gln Ser His
1               5                   10                  15

Met Ala Pro Thr His Gln Leu Pro Pro Ser Asp Val Arg Lys Ile Ile
            20                  25                  30

Leu Glu Leu Gln Pro Leu Ser Arg Gly Leu Leu Glu Asp Tyr Gln Lys
        35                  40                  45

Lys Glu Thr Gly Val Pro Glu Ser Asn Arg Thr Leu Leu Leu Cys Leu
    50                  55                  60

Thr Ser Asp Ser Gln Pro Pro Arg Leu Asn Ser Ser Ala Ile Leu Pro
65                  70                  75                  80

Tyr Phe Arg Ala Ile Arg Pro Leu Ser Asp Lys Asn Ile Ile Asp Lys
                85                  90                  95

Ile Ile Glu Gln Leu Asp Lys Leu Lys Phe Gln His Glu Pro Glu Thr
            100                 105                 110

Glu Ile Ser Val Pro Ala Asp Thr Phe Glu Cys Lys Ser Phe Ile Leu
        115                 120                 125

Thr Ile Leu Gln Gln Phe Ser Ala Cys Leu Glu Ser Val Phe Lys Ser
    130                 135                 140

Leu Asn Ser Gly Pro Gln
145                 150


<210> SEQ ID NO 28
<211> LENGTH: 149
<212> TYPE: PRT
<213> ORGANISM: artificial sequence
<220> FEATURE:
<223> OTHER INFORMATION: cIL-31-A/His6/TEV

<400> SEQUENCE: 28

Ala His His His His His His Glu Asn Leu Tyr Phe Gln Ser His Met
1               5                   10                  15

Ala Pro Thr His Gln Leu Pro Pro Ser Asp Val Arg Lys Ile Ile Leu
            20                  25                  30

Glu Leu Gln Pro Leu Ser Arg Gly Leu Leu Glu Asp Tyr Gln Lys Lys
        35                  40                  45

Glu Thr Gly Val Pro Glu Ser Asn Arg Thr Leu Leu Leu Cys Leu Thr
    50                  55                  60

Ser Asp Ser Gln Pro Pro Arg Leu Asn Ser Ser Ala Ile Leu Pro Tyr
65                  70                  75                  80

Phe Arg Ala Ile Arg Pro Leu Ser Asp Lys Asn Ile Ile Asp Lys Ile
                85                  90                  95

Ile Glu Gln Leu Asp Lys Leu Lys Phe Gln His Glu Pro Glu Thr Glu
```

```
            100                 105                 110

Ile Ser Val Pro Ala Asp Thr Phe Glu Cys Lys Ser Phe Ile Leu Thr
        115                 120                 125

Ile Leu Gln Gln Phe Ser Ala Cys Leu Glu Ser Val Phe Lys Ser Leu
    130                 135                 140

Asn Ser Gly Pro Gln
145


<210> SEQ ID NO 29
<211> LENGTH: 139
<212> TYPE: PRT
<213> ORGANISM: artificial sequence
<220> FEATURE:
<223> OTHER INFORMATION: cIL-31/A/C

<400> SEQUENCE: 29

Met Ala Ser His Met Ala Pro Thr His Gln Leu Pro Pro Ser Asp Val
1               5                   10                  15

Arg Lys Ile Ile Leu Glu Leu Gln Pro Leu Ser Arg Gly Leu Leu Glu
            20                  25                  30

Asp Tyr Gln Lys Lys Glu Thr Gly Val Pro Glu Ser Asn Arg Thr Leu
        35                  40                  45

Leu Leu Cys Leu Thr Ser Asp Ser Gln Pro Pro Arg Leu Asn Ser Ser
    50                  55                  60

Ala Ile Leu Pro Tyr Phe Arg Ala Ile Arg Pro Leu Ser Asp Lys Asn
65                  70                  75                  80

Ile Ile Asp Lys Ile Ile Glu Gln Leu Asp Lys Leu Lys Phe Gln His
                85                  90                  95

Glu Pro Glu Thr Glu Ile Ser Val Pro Ala Asp Thr Phe Glu Cys Lys
            100                 105                 110

Ser Phe Ile Leu Thr Ile Leu Gln Gln Phe Ser Ala Cys Leu Glu Ser
        115                 120                 125

Val Phe Lys Ser Leu Asn Ser Gly Pro Gln Cys
    130                 135


<210> SEQ ID NO 30
<211> LENGTH: 138
<212> TYPE: PRT
<213> ORGANISM: artificial sequence
<220> FEATURE:
<223> OTHER INFORMATION: cIL-31/AoM/C

<400> SEQUENCE: 30

Ala Ser His Met Ala Pro Thr His Gln Leu Pro Pro Ser Asp Val Arg
1               5                   10                  15

Lys Ile Ile Leu Glu Leu Gln Pro Leu Ser Arg Gly Leu Leu Glu Asp
            20                  25                  30

Tyr Gln Lys Lys Glu Thr Gly Val Pro Glu Ser Asn Arg Thr Leu Leu
        35                  40                  45

Leu Cys Leu Thr Ser Asp Ser Gln Pro Pro Arg Leu Asn Ser Ser Ala
    50                  55                  60

Ile Leu Pro Tyr Phe Arg Ala Ile Arg Pro Leu Ser Asp Lys Asn Ile
65                  70                  75                  80

Ile Asp Lys Ile Ile Glu Gln Leu Asp Lys Leu Lys Phe Gln His Glu
                85                  90                  95

Pro Glu Thr Glu Ile Ser Val Pro Ala Asp Thr Phe Glu Cys Lys Ser
            100                 105                 110
```

-continued

```
Phe Ile Leu Thr Ile Leu Gln Gln Phe Ser Ala Cys Leu Glu Ser Val
        115                 120                 125

Phe Lys Ser Leu Asn Ser Gly Pro Gln Cys
    130                 135
```